United States Patent [19]
Carlson et al.

[11] Patent Number: 5,973,228
[45] Date of Patent: Oct. 26, 1999

[54] CONIFERIN BETA-GLUCOSIDASE CDNA FOR MODIFYING LIGNIN CONTENT IN PLANTS

[75] Inventors: John E. Carlson, Port Matilda, Pa.; D. Palitha Dharmawardhana, Vancouver, Canada; Carl J. Douglas, Vancouver, Canada; Brian E. Ellis, Vancouver, Canada

[73] Assignee: University of British Columbia, Vancouver, Canada

[21] Appl. No.: 09/122,230

[22] Filed: Jul. 23, 1998

Related U.S. Application Data

[60] Provisional application No. 60/053,566, Jul. 24, 1997.

[51] Int. Cl.$^6$ ............................. C12N 5/04; C12N 15/29; C12N 15/82; A01H 7/00
[52] U.S. Cl. ...................... 800/298; 435/320.1; 435/419; 435/468; 536/23.6; 536/24.5; 800/278; 800/290; 800/319; 800/286
[58] Field of Search ................. 435/69.1, 320.1, 435/410, 419, 468; 536/23.6, 24.5; 800/278, 286, 290, 295, 298, 319

[56] References Cited

U.S. PATENT DOCUMENTS

| | | | |
|---|---|---|---|
| 5,451,514 | 9/1995 | Boudet et al. | 435/468 |
| 5,583,021 | 12/1996 | Dougherty et al. | 435/468 |
| 5,608,148 | 3/1997 | John | 800/278 |
| 5,633,439 | 5/1997 | Walter | 800/278 |
| 5,850,020 | 12/1998 | Bloksberg et al. | 800/278 |
| 5,866,791 | 2/1999 | Holt | 800/278 |

FOREIGN PATENT DOCUMENTS

| | | | |
|---|---|---|---|
| 2005597 | 6/1990 | Canada | C12N 15/00 |
| WO 94/23044 | 10/1994 | WIPO | C12N 15/82 |

OTHER PUBLICATIONS

Binns et al., Cell division promoting activity of naturally occuring dehydrodiconiferyl glucosides: Do cell wall components control cell division? *Proc. Natl. Acad. Sci., USA* 84:980–984 (1987).

Campbell and Sederoff, Variation in lignin content and compositon, *Plant Physiol.* 110:3–13 (1996).

Dwivedi et al., Modification of lignin biosynthesis in transgenic Nicotiana through expression of an antisense O–methyltransferase gene from Populus, *Plant Molecular Biology* 26:61–71 (1994).

Sederoff et al., Genetic regulation of lignin biosynthesis and the potential modification of wood by genetic engineering in loblolly pine (Chapter 12), in *Genetic Engineering of Plant Secondary Metabolism* (Ellis et al., Eds.) Plenum Press, New York (1994).

Stam et al, Annals of Botany, vol. 79, pp. 3–12, 1997.

Branch, A.D., Trends in Biochem. Sci., vol. 23, pp. 45–50, 1998.

van der Krol et al, Gene, vol. 72, pp. 45–50, 1988.

Smith et al, Plant Cell, vol. 6, pp. 1441–1453, 1994.

Dharmawardhana et al., A β–Glucosidase from Lodgepole Pine Xylem Specific for the Lignin Precursor Coniferin, *Plant Physiology* 107:331–339 (1995).

Elkind et al., Abnormal Plant Development and Down-–Regulation of Phenylpropanoid Biosynthesis in Transgenic Tobacco Containing a Heterologous Phenylalanine Ammonia–lyase Gene, *Proc. Natl. Acad. Sci., USA* 87:9057–9061 (1990).

Lee, D. and Douglas, C.J., Antisense and Sense Suppression of 4–Coumarate:CoA Ligase (4CL) in Tobacco and Arabidopsis, *Plant Physiology* Suppl. 105:37. Abstract.

Leinhos et al., Purification of an Acidic Coniferin–Hydrolysing β–Glucosidase from Developing Xylem of *Pinus Banksiana*, *Phytochemistry* 37:311–315 (1994).

Genbank Protein Database Accession No. 1236961.
Genbank Protein Database Accession No. 833835.
Genbank Protein Database Accession No. 1362162.
Genbank Protein Database Accession No. 114975.
Genbank Protein Database Accession No. 114974.
Genbank Protein Database Accession No. 112564.
Genbank Protein Database Accession No. 1127575.
Genbank Protein Database Accession No. 1076712.
Genbank Protein Database Accession No. 1374991.

*Primary Examiner*—Elizabeth F. McElwain
*Assistant Examiner*—Ashwin D. Mehta
*Attorney, Agent, or Firm*—Klarquist Sparkman Campbell Leigh & Whinston, LLP

[57] ABSTRACT

A cDNA molecule encoding coniferin beta-glucosidase is disclosed. This enzyme catalyzes one of the last steps in the synthesis of lignin in plants. Plants having modified lignin content may be produced by transformation with this cDNA (or parts of the cDNA), for example, in either sense or antisense orientation. The invention includes methods of altering-lignin content in plants using this cDNA, as well as transformed plants, such as conifers, having modified lignin content.

40 Claims, 3 Drawing Sheets

```
GGATTTGGACCTGAAAATATCAATTTCAAAGCAATTCCAGAGGGATAACGTGGGATCCTTACCATTACCAAC

AACCCACCATTCCGCCCTGCCGACCTCAGGCATATTTTGATTCTATTTAACCATTAATTCATCTGGGCAGTT

GTGATTCTGTATAATTCGATCGCTCCGTTTTAGCAGACATGGAGGTGTCTGTGTTGATGTGGGTACTGCTCT
                                     M  E  V  S  V  L  M  W  V  L  L
TCTATTCCTTATTAGGTTTTCAAGTGACGACAGCTAGGCTGGACAGGAACAACTTCCCCTCAGATTTCATGT
 F  Y  S  L  L  G  F  Q  V  T  T  A  R  L  D  R  N  N  F  P  S  D  F  M
TCGGCACAGCCTCTTCAGCGTATCAGTATGAAGGAGCAGTCCGAGAAGATGGCAAGGGTCCTAGCACATGGG
 F  G  T  A  S  S  A  Y  Q  Y  E  G  A  V  R  E  D  G  K  G  P  S  T  W
ACGCCTTAACACATATGCCTGGTAGAATAAAAGATAGCAGCAATGGAGACGTGGCAGTCGACCAATATCACA
 D  A  L  T  H  M  P  G  R  I  K  D  S  S  N  G  D  V  A  V  D  Q  Y  H
GATATATGGAAGATATCGAGCTTATGGCTTCACTTGGACTAGATGCCTATAGATTCTCCATATCCTGGTCTC
 R  Y  M  E  D  I  E  L  M  A  S  L  G  L  D  A  Y  R  F  S  I  S  W  S
GAATCCTTCCAGAAGGAAGAGGTGAAATTAACATGGCTGGGATTGAATATTACAATAATCTGATTGACGCTC
 R  I  L  P  E  G  R  G  E  I  N  M  A  G  I  E  Y  Y  N  N  L  I  D  A
TTCTGCAAAATGGGATCCAGCCGTTCGTGACATTGTTCCATTTCGATCTTCCCAAAGCACTTGAAGACTCCT
 L  L  Q  N  G  I  Q  P  F  V  T  L  F  H  F  D  L  P  K  A  L  E  D  S
ATGGGGGATGGCTGAGTCCTCAAATAATTAACGACTTCGAAGCCTATGCAGAGATTTGCTTCCGGGCATTCG
 Y  G  G  W  L  S  P  Q  I  I  N  D  F  E  A  Y  A  E  I  C  F  R  A  F
GTGACCGTGTCAAATATTGGGCGACAGTGAACGAGCCAAATCTGTTTGTGCCGTTGGGATACACCGTCGGAA
 G  D  R  V  K  Y  W  A  T  V  N  E  P  N  L  F  V  P  L  G  Y  T  V  G
TATTTCCACCGACGAGGTGTGCTGCCCCTCACGCCAATCCTTTGTGCATGACAGGGAATTGCTCGTCAGCAG
 I  F  P  P  T  R  C  A  A  P  H  A  N  P  L  C  M  T  G  N  C  S  S  A
AGCCATATCTAGCTGCACATCACGTTTTGCTCGCCCACGCATCTGCAGTGGAGAAATATAGGGAGAAATATC
 E  P  Y  L  A  A  H  H  V  L  L  A  H  A  S  A  V  E  K  Y  R  E  K  Y
AGAAAATTCAAGGAGGATCTATAGGGTTAGTTATAAGCGCGCCATGGTACGAACCCTTGGAAAATTCTCCAG
 Q  K  I  Q  G  G  S  I  G  L  V  I  S  A  P  W  Y  E  P  L  E  N  S  P
AAGAGAGATCAGCTGTTGATAGAATTTTATCCTTCAATCTCCGATGGTTTTTGGATCCAATTGTTTTTGGAG
 E  E  R  S  A  V  D  R  I  L  S  F  N  L  R  W  F  L  D  P  I  V  F  G
ATTATCCACAAGAAATGCGTGAAAGATTAGGATCGCGCTTACCCTCCATATCCTCGGAACTATCTGCGAAAC
 D  Y  P  Q  E  M  R  E  R  L  G  S  R  L  P  S  I  S  S  E  L  S  A  K
TTCGGGGATCGTTCGACTATATGGGTATTAATCACTATACAACCTTATATGCAACAAGCACTCCTCCCCTTT
 L  R  G  S  F  D  Y  M  G  I  N  H  Y  T  T  L  Y  A  T  S  T  P  P  L
CCCCCGACCACACGCAATATCTATATCCAGACTCTAGGGTTTATCTGACTGGAGAGCGCCACGGAGTCTCCA
 S  P  D  H  T  Q  Y  L  Y  P  D  S  R  V  Y  L  T  G  E  R  H  G  V  S
TCGGAGAACGGACAGGGATGGACGGTTTGTTTGTGGTACCTCATGGAATTCAAAAAATAGTGGAGTATGTAA
 I  G  E  R  T  G  M  D  G  L  F  V  V  P  H  G  I  Q  K  I  V  E  Y  V
AAGAATTCTATGACAACCCGACTATTATTATCGCAGAGAACGGTTATCCAGAGTCTGAGGAATCCTCGTCGA
 K  E  F  Y  D  N  P  T  I  I  I  A  E  N  G  Y  P  E  S  E  E  S  S  S
CTCTGCAAGAAAATCTAAACGATGTGAGGAGAATAAGGTTTCATGGAGATTGTTTGAGTTATCTCAGTGCAG
 T  L  Q  E  N  L  N  D  V  R  R  I  R  F  H  G  D  C  L  S  Y  L  S  A
CAATCAAAAATGGCTCAGATGTTCGAGGGTACTTTGTGTGGTCACTTCTGGATAATTTTGAGTGGGCATTTG
 A  I  K  N  G  S  D  V  R  G  Y  F  V  W  S  L  L  D  N  F  E  W  A  F
GGTATACCATTAGATTTGGTCTTTATCACGTGGATTTCATTTCTGATCAAAAGAGATATCCCAAGCTCTCGG
 G  Y  T  I  R  F  G  L  Y  H  V  D  F  I  S  D  Q  K  R  Y  P  K  L  S
CTCAATGGTTCAGACAATTTCTTCAGCACGACGATCAGGGAAGTATTAGAAGCAGCAGCAGCATTTAGACTG
 L  N  G  S  D  N  F  F  S  T  T  I  R  E  V  L  E  A  A  A  A  F  R  L
 A  Q  W  F  R  Q  F  L  Q  H  D  D  Q  G  S  I  R  S  S  S  I  -
CGTTGTCTATTTGCTAATCAAAGCGCACACATTCCTGCAACTCTACCCAAAATCCTGCAAGCAAATATGTTG

TGTTCGGATCTATCCACCGTGAGACACATTACAAAGAAATCATCAATCTATTCCAAAATGCAGAAAACCCCA

TTCAGATGTTCTAGGGAACTGCAGGGTAAGAACATTG
```

FIG. 1

CONIFERIN BETA-GLUCOSIDASE CDNA FOR MODIFYING LIGNIN CONTENT IN PLANTS

CROSS REFERENCE TO RELATED APPLICATION

This application claims priority to U.S. Provisional Patent Application Ser. No. 60/053,566, filed Jul. 24, 1997, which is incorporated herein by reference.

TECHNICAL FIELD

This invention relates to DNA molecules cloned from plants and methods of using such DNA molecules to produce transgenic plants with altered lignin content.

BACKGROUND

Lignin is the second most abundant organic material in the biosphere, and is a major component of cell walls of woody plants (such as poplar and pine species) and fodder crops (such as maize, wheat and barley). The quantity of lignin in plant material affects characteristics that are agronomically important. For example, in fodder crops the amount of lignin present determines how easily the crop may be digested by animals; relatively small increases in lignin content may produce large decreases in the digestibility of the crop. Therefore, reducing lignin content would enhance digestibility, facilitating a more efficient use of such crops. In the timber industry, producing wood pulp for papermaking requires the removal of lignin to release the cellulosic content of the timber. The process of removing the lignin consumes large amounts of energy and produces environmentally harmful lignin waste liquors which must be treated prior to disposal. It has also been suggested that residual lignin in paper pulp may produce toxic polychlorinated biphenols when the lignin interacts with chlorine used in the bleaching process. Thus, decreasing lignin content in wood products would be advantageous for papermaking. On the other hand, increasing the lignin content of timber offers the possibility of increased wood strength.

Accordingly, modification of quality and quantity of lignin in plants has been a long-standing interest among breeders and, more recently, among molecular biologists. Recent molecular approaches towards methods for reducing lignin content in plants are typified by: U.S. Pat. No. 5,451,514, "Modification of Lignin Synthesis in Plants"; Canadian Patent No. 2,005,597, "Plants Having Reduced Lignin or Lignin of Altered Quality"; and International Patent Application Publication No. WO 94/23044.

Lignin is a complex polymer of three cinnamyl alcohols, p-coumaryl, coniferyl and sinapyl, all products of phenylpropanoid metabolism. Depending on the plant species or tissue, the relative proportion of the different monomers in lignin can vary significantly. In gymnosperms for example, lignin is predominantly composed of coniferyl alcohol monomer units, whereas angiosperms have significant proportions of sinapyl moieties. The metabolism of lignin production involves many intermediates, enzymatic pathways and, correspondingly, genes. Accordingly, there are several gene/enzyme targets that might be selected to manipulate lignin production through genetic engineering.

Alteration of lignin levels by antisense and sense suppression of gene expression has already been attempted for several enzymes in the phenylpropanoid pathway including PAL (Elkind et al. 1990), CAD (Schuch 1993; Canadian patent 2,005,597; U.S. Pat. No. 5,541,514), 4CL (Lee and Douglas 1994) and COMT (WO 94/23044). However, all of these attempts to modify lignin synthesis are directed at early stages in the synthetic pathway and are therefore likely to interfere with other metabolic processes which share these intermediate steps. It is clear, for example, that interference with early steps in the phenylpropanoid pathway can have undesirable pleiotropic effects (Elkind et al., 1990). In addition, modulating biosynthetic enzymes that act early in the pathway may not be effective because alternative synthetic routes may be available. A better approach to modulating lignin synthesis would be to regulate later stages in the lignin biosynthesis pathway: this would minimize or avoid pleiotropic effects and would likely provide a greater degree of effective control.

The present invention is directed towards the identification of a gene that regulates a later step in the lignin biosynthesis pathway, and the use of this gene to modify lignin content in plants.

SUMMARY OF THE INVENTION

The inventors have determined that the gene encoding coniferin beta-glucosidase would be an excellent target gene for modifying lignin content in plants, particularly in trees such as conifers. The coniferin beta-glucosidase enzyme catalyzes the hydrolysis of the 4-O-glucoside of coniferyl alcohol, coniferin, which is one of the last steps in the biosynthesis of lignin. Thus, the level of coniferin beta-glucosidase activity directly affects lignin synthesis and, therefore, the quantity of lignin in the plant tissue. Coniferin accumulates in conifer xylem during cambium reactivation, consistent with a role as the dominant lignin precursor in these species (Freudenberg and Harkin 1963, Savidge 1989). Beta-glucosidases capable of hydrolyzing coniferin have been detected in suspension culture systems (Hosel et al. 1982, Hosel and Todenhagen 1980) and seedlings (Marcinowski and Grisebach 1978), and a coniferin beta-glucosidase has been purified from differentiating xylem in trees (Dharmawardhana et al., 1995). However, to date, the genetic manipulation of coniferin beta-glucosidase has not been possible because the gene encoding the enzyme has not been cloned.

To that end, the inventors have cloned and sequenced a complementary DNA (cDNA) sequence from the conifer tree species *Pinus contorta*. The provision of this cDNA sequence enables, for the first time, the regulation of coniferin beta-glucosidase activity in plants through genetic engineering. Specifically, the invention provides genetic constructs, such as plant transformation vectors, that include various forms of the coniferin beta-glucosidase cDNA or sequences that are homologous to this cDNA. Depending on the specific nature of these constructs, they may be introduced into plants in order to increase or reduce the production of the coniferin beta-glucosidase enzyme, and therefore to regulate lignin synthesis.

Transformation vectors according to this invention preferably include a recombinant DNA sequence that comprises all or part of the coniferin beta-glucosidase cDNA. Depending on the nature of the promoter sequence selected, such constructs may be used to modify lignin content throughout the plant or in a tissue-specific manner and either constitutively or at certain stages of plant development. The availability of inducible plant promoters also offers the possibility of changing lignin biosynthesis in a plant at desired times by application of the chemical or physical agent that induces transcription from the promoter.

In one embodiment, transformation vectors may be constructed to over-express the coniferin beta- glucosidase enzyme ("sense" orientation). Enhanced lignin synthesis may be achieved by introducing such vectors into plants. Examples of the application of this approach to modify plant phenotypes include U.S. Pat. No. 5,268,526, "Overexpression of Phytochrome in Transgenic Plants", U.S. Pat. No. 4,795,855, "Transformation and Foreign Gene Expression in Woody Species", and U.S. Pat. No. 5,443,974 (overexpression of stearoyl-ACP desaturase gene).

Alternatively, such over-expression vectors may be used to suppress coniferin beta-glucosidase enzyme activity through sense-suppression, as described in U.S. Pat. Nos. 5,034,323 and 5,283,184, both entitled "Genetic Engineering of Novel Plant Phenotypes".

In another embodiment, constructs may be designed to express plus-sense untranslatable coniferin beta-glucosidase RNA, using methodologies described in U.S. Pat. No: 5,583,021, "Production of Virus Resistant Plants". Constructs of this type may be used to reduce the expression of the native coniferin beta-glucosidase gene, thereby reducing coniferin beta-glucosidase enzyme activity and, as a result, lignin content.

In other embodiments, the present invention provides genetic constructs designed to express antisense versions of the coniferin beta-glucosidase RNA. "Antisense" RNA is an RNA sequence that is the reverse complement of the mRNA encoded by a target gene. Examples of the use of antisense RNA to inhibit expression of target plant genes include U.S. Pat. No. 5,451,514, "Modification of Lignin Synthesis in Plants" (use of antisense RNA to regulate CAD), U.S. Pat. No. 5,356,799, "Antisense Gene Systems of Pollination Control for Hybrid Seed Production", U.S. Pat. No. 5,530, 192 (use of antisense RNA to alter amino acid and fatty acid composition in plants).

In conjunction with these genetic constructs, the present invention also includes methods for altering lignin biosynthesis in plants. Generally, such methods comprise introducing into the genome of a plant a genetic construct that includes all or part of the coniferin beta-glucosidase cDNA (either in sense or antisense orientation) or a sequence derived from this cDNA. Methods for introducing transformation vectors into plants are well known in the art and include electroporation of plant protoplasts, liposome-mediated transformation, polyethylene mediated transformation; transformation using viruses, micro-injection of plant cells, micro-projectile bombardment of plant cells, vacuum infiltration, and *Agrobacterium tumeficiens* (AT) mediated transformation. Methods particularly suited to the transformation of woody species are described in Ellis et al. (1993), Ellis et al. (1996), U.S. Pat. No. 5,122,466, "Ballistic Transformation of Conifer" and U.S. Pat. No. 4,795,855, "Transformation and Foreign Gene Expression with Woody Species".

The invention also includes transformed plants having altered lignin compositions as a result of being transformed with a genetic construct as described above. Examples of plants that may be transformed in this manner include conifers, such as plants from the genera Picea, Pseudotsuga, Tsuga, Sequoia, Abies, Thuja, Libocedrus, Chamaecyparis and Laryx. Pines are expected to be a particularly suitable choice for genetic modification by the methods disclosed herein, including loblolly pine (*Pinus taeda*), slash pine (*Pinus elliotii*), longleaf pine (*Pinus palustris*), shortleaf pine (*Pinus echinata*), jack pine (*Pinus banksiana*), ponderosa pine (*Pinus ponderosa*), red pine (*Pinus resinosa*), Eastern white pine (*Pinus strobus*), Western white pine (*Pinus monticola*), sugar pine (*Pinus lambertiana*), lodgepole pine (*Pinus contorta*), Monterey pine (*Pinus radiata*), Afghan pine (*Pinus eldarica*), Scots pine (*Pinus sylvestris*) and Virginia pine (*Pinus virginiana*). Other tree species, including poplar, eucalyptus and aspen may also be transformed using the nucleotide sequences of this invention. However, the invention is not limited to trees: crop and forage plants such as maize, tobacco, alfalfa, wheat and grasses may also be transformed using the constructs provided by this invention in order to modify lignin content. In general, this invention can be applied to any plant species that can be transformed.

BRIEF DESCRIPTION OF THE DRAWINGS

FIG. 1 shows the nucleic acid sequence of the coniferin beta-glucosidase cDNA and the amino acid sequence of the encoded protein.

DETAILED DESCRIPTION OF THE INVENTION

Definitions and Abbreviations

Figure 2:
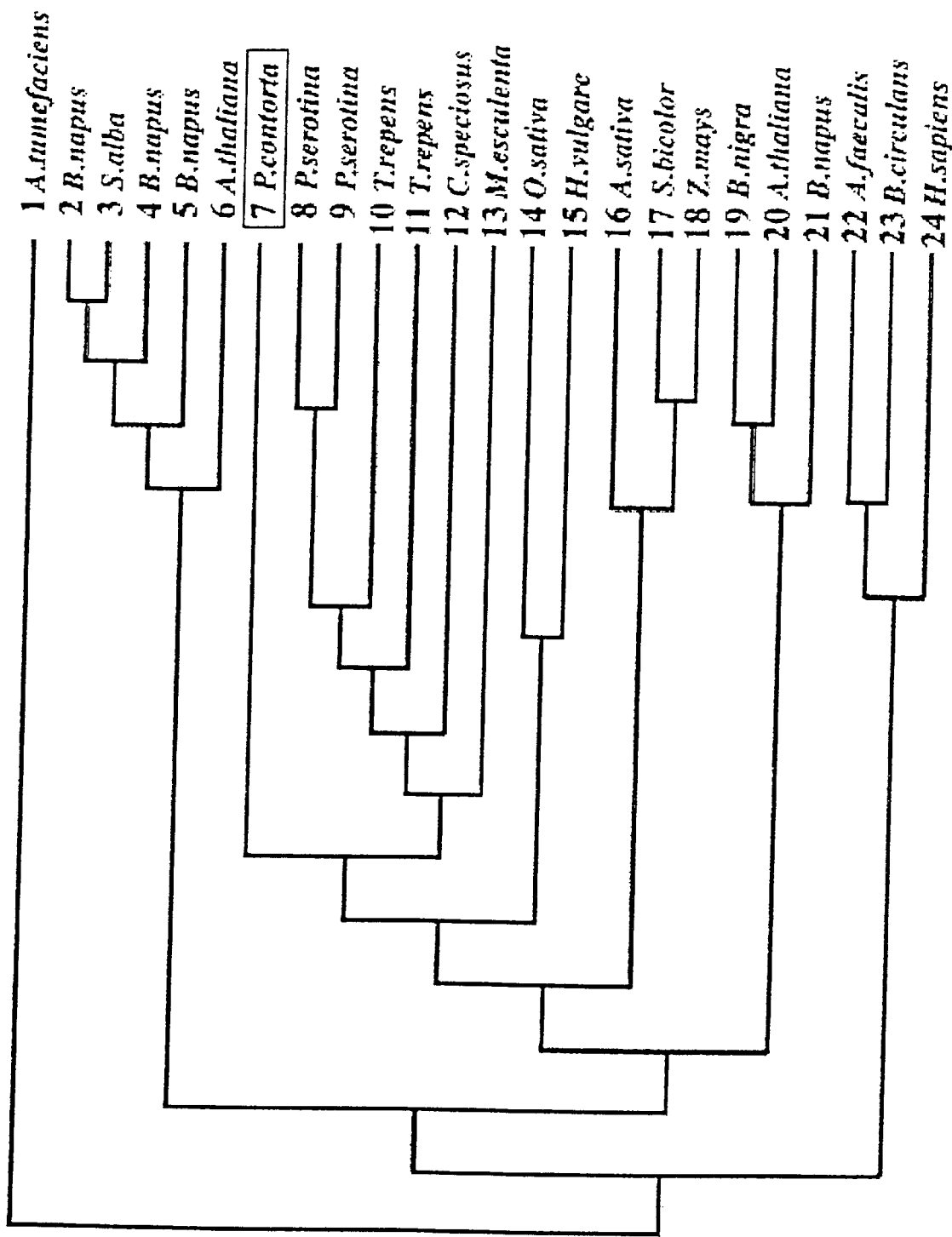
FIG. 2 is a dendrogram illustrating the amino acid sequence comparisons between plant, two bacterial and one human family 1 glycosyl hydrolases and a family 3 glycosyl hydrolase from *Agrobacterium tumefaciens*. The dendrogram was constructed using GeneWorks CLUSTAL V program. Database accession numbers are in parentheses. 1, *A. tumefaciens* coniferin β-G (a42292); 2, *Brassica napus* thio β-G (q00326); 3, *Sinapis alba* thio β-G (p29092); 4, *B. napus* thio β-G (s56656); 5, *B.napus* thio β-G (s39549); 6, *Arabidopsis thaliana* thio β-G (p37702); 7, *Pinus contorta* coniferin β-G; 8, *Prunus serotina* cyanogenic β-G (u50201); 9, *Prunus serotina* cyanogenic β-G (u26025); 10, *Trifolium repens* cyanogenic β-G (p26205); 11, *T. repens* β-G (26204); 12, *Costus speciosus* furostanol 26-O-β-G (d83177); 13, *Manihot esculenta* cyanogenic β-G (s23940); 14, *Oryza sativa* cyanogenic β-G (u28047); 15, *Hordeum vulgare* cyanogenic β-G (a57512); 16, *Avena sativa* β-G (s50756); 17, *Sorghum bicolor* cyanogenic β-G (u33817); 18, *Zea mays* β-G (p49235); 19, *Brassica nigra* β-G (u72154); 20, *A. thaliana* β-G (u72153); 21, *B.napus* β-G (s52771); 22, *Agrobacterium faecalis* cellobiase (g67489); 23, *Bacillus circulans* cellobiase (q03506); 24, *Homo sapiens* lactase-phlorizin hydrolase domain IV (p09848).

The following abbreviations are used herein:
4-NPG: 4-nitrophenyl β-glucoside
2-NPG: 2-nitrophenyl β-glucoside
MUG: 4-methylumbelliferyl β-glucoside
VRA-G: 5,4-( β-D-glucopyranosyloxy)-3- methoxyphenyl-methylene -2-thioxothiazolidin-4-one-3-ethanoic acid.
VRA-G is a substrate analog of coniferin synthesized by Biosynth International Inc., Skoke, Ill.
EDC: 1-ethyl-3-(dimethylaminopropyl) carbodiimide
PAL: phenylalanine anunonia-lyase
CAD: Cinnamyl alcohol dehydrogenase
4CL: 4-coumarate: CoA ligase
COMT: caffeic acid 3-o-methyltransferase
PAGE: polyacrylamide gel electrophoresis
CBG: coniferin β-glucosidase Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of*

*Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following definitions of terms are provided:

Coniferin Beta-glucosidase Biological Activity

The defining functional characteristic of the coniferin beta-glucosidase enzyme is its ability to hydrolyze coniferin to release coniferyl alcohol. This activity can be measured using the glucosidase assay described herein. Thus, a protein having coniferin beta-glucosidase biological activity is a protein that is able to hydrolyze coniferin to release coniferyl alcohol in the described assay.

Coniferin Beta-glucosidase (CBG) Protein

A protein having coniferin beta-glucosidase biological activity and sharing amino acid sequence identity with the amino acid sequence of the prototypical coniferin beta-glucosidase protein shown in Seq. I.D. No. 7. (the Pinus CBG protein). CBG proteins that are more distantly related to the prototypical CBG protein will share at least 50% amino acid sequence identity with the sequence shown in Seq. I.D. No. 7, as determined by the methods described below. More closely related CBG proteins may share at least 60%, 65%, 70%, 75% or 80% sequence identity with the Pinus CBG protein. CBG proteins that are most closely related to the Pinus protein will have CBG protein biological activity and share at least 85%, 90% or 95% sequence identity with the Pinus protein.

CBG gene/ CBG cDNA

Nucleic acid molecules that encode a CBG protein. Nucleic acid molecules that encode the Pinus CBG protein are provided in Seq. I.D. No. 6 (Pinus CBG CDNA), and Seq. I.D. No. 8 (Pinus CBG ORF). The invention includes not only the nucleic acid molecules provided in Seq. I.D. Nos. 6 and 8, but also homologs and orthologs of these sequences, nucleic acid molecules that encode CBG proteins, and probes and primers that are derived from these sequences.

Probes and Primers

Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acids, preferably DNA oligo-nucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (1989), Ausubel et al. (1987), and Innis et al., (1990). PCR primer pairs can be derived from a known sequence, for example, by using computer programs intended for that purpose such as Primer (Version 0.5, ©1991, Whitehead Institute for Biomedical Research, Cambridge, Mass. One of skill in the art will appreciate that the specificity of a particular probe or primer increases with its length. Thus, for example, a primer comprising 20 consecutive nucleotides of the Pinus CBG cDNA will anneal to a target sequence such as a CBG gene homolog from eucalyptus contained within a eucalyptus cDNA library with a higher specificity than a corresponding primer of only 15 nucleotides. Thus, in order to obtain greater specificity, probes and primers may be selected that comprise 20, 25, 30, 35, 40, 50 or more consecutive nucleotides of the Pinus CBG cDNA or gene sequences.

The invention thus includes isolated nucleic acid molecules that comprise specified lengths of the disclosed CBG cDNA sequence. Such molecules may comprise at least 20, 25, 30, 35, 40 or 50 consecutive nucleotides of these sequences and may be obtained from any region of the disclosed sequences. By way of example, the Pinus CBG cDNA sequences may be apportioned into halves or quarters based on sequence length, and the isolated nucleic acid molecule may be derived from the first or second halves of the molecule, or any of the four quarters. The Pinus CBG cDNA, shown in Seq. I.D. No. 6 may be used to illustrate this. The Pinus CBG cDNA is 1909 nucleotides in length and so may be hypothetically divided into halves (nucleotides 1–955 and 956–1909) or quarters (nucleotides 1–477, 478–955, 956–1433 and 1434–1909). Nucleic acid molecules may be selected that comprise at least 20, 25, 30, 35, 40 or 50 consecutive nucleotides of any of these portions of the Pinus cDNA. Thus, one such nucleic acid molecule might comprise at least 25 consecutive nucleotides of the region comprising nucleotides 1–955 of the disclosed Pinus cDNA.

Sequence Identity the similarity between two nucleic acid sequences, or two amino acid sequences is expressed in terms of the similarity between the sequences, otherwise referred to as sequence identity. Sequence identity is frequently measured in terms of percentage identity (or similarity or homlogy); the higher the percentage, the more similar the two sequences are. Homologs of the Pinus CBG protein will possess a relatively high degree of sequence identity when aligned using standard methods.

Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at htp://www.ncbi.nlm.nih.gov/BLAST/. A description of how to determine sequence identity using this program is available at http://www.ncbi.nlm.nih.gov/BLAST/blast help.html.

Homologs of the disclosed Pinus CBG protein are typically characterized by possession of at least 50% sequence identity counted over the full length alignment with the amino acid sequence of Pinus CBG using the NCBI Blast 2.0, gapped blastp set to default parameters. Proteins with even greater similarity to the reference sequences will show increasing percentage identities when assessed by this method, such as at least 60%, at least 65%, at least 70%, at least 75%, at least 80%, at least 90% or at least 95% sequence identity. When less than the entire sequence is being compared for sequence identity, homologs will typically possess at least 75% sequence identity over short windows of 10–20 amino acids, and may possess sequence identities of at least 85% or at least 90% or 95% depending on their similarity to the reference sequence. Methods for determining sequence identity over such short windows are described at http://www.ncbi.nlm. nih.gov/BLAST/blast FAQs.html. One of skill in the art will appreciate that these sequence identity ranges are provided for guidance only; it is entirely possible that strongly significant homologs could be obtained that fall outside of the ranges provided. The present invention provides not only the peptide homologs are described above, but also nucleic acid molecules that encode such homologs.

An alternative indication that two nucleic acid molecules are closely related is that the two molecules hybridize to each other under stringent conditions. Stringent conditions are sequence dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (1989) and Tijssen (1993). Nucleic acid molecules that hybridize under stringent conditions to the Pinus CBG sequences will typically hybridize to a probe based on either the entire Pinus CBG cDNA or selected portions of the cDNA under wash conditions of 0.2×SSC, 0.1% SDS at 65° C.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequence that all encode substantially the same protein.

Specific Binding Agent

An agent that binds substantially only to a defined target. Thus a CBG protein specific binding agent binds substantially only the CBG protein. As used herein, the term "CBG protein specific binding agent" includes anti-CBG protein antibodies and other agents that bind substantially only to the CBG protein. Anti-CBG protein antibodies may be produced using standard procedures described in a number of texts, including Harlow and Lane (1988). The determination that a particular agent binds substantially only to the CBG protein may readily be made by using or adapting routine procedures. One suitable in vitro assay makes use of the Western blotting procedure (described in many standard texts, including Harlow and Lane (1988)). Western blotting may be used to determine that a given CBG protein binding agent, such as an anti-CBG protein monoclonal antibody, binds substantially only to the CBG protein.

Oligonucleotide

A linear polynucleotide sequence of up to about 100 nucleotide bases in length.

Vector

A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Transformed

A transformed cell is a cell into which has been introduced a nucleic acid molecule by molecular biology techniques. As used herein, the term transformation encompasses all techniques by which a nucleic-acid molecule might be introduced into such a cell, including transfection with viral vectors, transformation with plasmid vectors, and introduction of naked DNA by electroporation, lipofection, and particle gun acceleration.

Isolated

An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Purified

The term purified does not require absolute purity; rather, it is intended as a relative term. Thus, for example, a purified CBG protein preparation is one in which the CBG protein is more enriched than the protein is in its natural environment within a cell. Generally, a preparation of CBG protein is purified such that the CBG represents at least 50% of the total protein content of the preparation. For particular applications, higher purity may be desired, such that preparations in which CBG represents at least 75% or at least 90% of the total protein content may be employed.

Ortholog

Two nucleotide or amino acid sequences are orthologs of each other if they share a common ancestral sequence and diverged when a species carrying that ancestral sequence split into two species. Orthologous sequences are also homologous sequences.

Operably Linked

A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Recombinant

A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

cDNA (Complementary DNA)

A piece of DNA lacking internal, non-coding segments (introns) and regulatory sequences that determine transcription. cDNA is synthesized in the laboratory by reverse transcription from messenger RNA extracted from cells.

ORF (Open Reading Frame)

A series of nucleotide triplets (codons) coding for amino acids without any termination codons. These sequences are usually translatable into a peptide.

Transgenic Plant

As used herein, this term refers to a plant that contains recombinant genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually).

Sequence Listing

The nucleic and amino acid sequences listed in the accompanying sequence listing are showed using standard letter abbreviations for nucleotide bases, and three letter code for amino acids. The letter "N" is used to indicate inosine in the nucleic acid sequences. Only one strand of each nucleic acid sequence is shown, but the complementary strand is understood as included by any reference to the displayed strand.

Seq. I.D. No. 1 is primer N7A
Seq. I.D. No. 2 is primer N7B
Seq. I.D. No. 3 is primer N10
Seq. I.D. No. 4 is primer CBG172
Seq. I.D. No. 5 is primer CBG75
Seq. I.D. No. 6 is the Pinus CBG cDNA
Seq. I.D. No. 7 is the Pinus CBG protein
Seq. I.D. No. 8 is the Pinus CBG ORF
Seq. I.D. No. 9 is primer NT1
Seq. I.D. No. 10 is primer CT1
Seq. I.D. Nos. 11–14 are primers useful for amplification of the CBG cDNA sequence.

Detailed aspects of the invention are provided in the following examples.

EXAMPLE 1

Identification of the Coniferin beta-glucosidase cDNA

Actively differentiating *Pinus contorta* xylem was harvested as described by Dharmwardhana et al. (1995) and used to isolate total RNA as described by Lewinsohn et al. (1994). PolyA RNA isolated with an Oligotex mRNA isolation kit (Qiagen) was used to construct a cDNA library in the λZAP-XR vector, employing Stratagene cDNA synthesis and GigapakII Gold packaging kits.

Coniferin beta-glucosidase enzyme was purified from *Pinus contorta* xylem tissue as described by Dharmwardhana et al. (1995). In order to determine the N-terminal amino acid sequence of the purified enzyme, it was run on native PAGE gels, stained for activity on the synthetic coniferin substrate VRA-G and the staining band excised and subjected to SDS-PAGE. The protein was then transferred to an Immobilon membrane for N-terminal amino acid sequencing using an Applied Biosystems 470A gas phase sequencer (Edman degradation).

Gene-specific primers for PCR amplification of CBG sequence fragments were then designed based on the 15 N-terminal amino acid sequence obtained. Primers N7A and N7B were based on the first 7 N-terminal amino acid residues and were identical except at the third base from the 3' end where the degeneracy is split between the primers. N7A: 5' GCTCTAGAGCGAC(T)A(C)GIAAC(T)AAC(T) TTTCC 3' (Seq. I.D. No. 1) N7B: 5' GCTCTAGAGCGAC (T)A(C)GIAAC(T)AAC(T)TTCCC 3' (Seq. I.D. No. 2) The amplification template used was the λZAP-cDNA library described above. The initial PCR reactions contained 200–300 ng λZAP-cDNA as template, 200 nM degenerate gene-specific primer N7A or N7B, 50 nM vector primer M13F or T7 (BRL), 200 M dNTP, and 1X reaction buffer (10 mM TrisHCl pH 8.3, 1.5 mM MgCl$_2$, 50 mM KCl) in a 50μl volume. Prior to adding 3 units Taq polymerase (Boehringer), the reaction mixture was heated to 94° C. for 2 min. The thermal cycling regime was as follows: 1–2 cycles (94° C./1 min., 48°–52° C./2 min., 72° /2 min.);30 cycles (94° C./45 sec., 55°/1 min., 72° C./2 min.); 72° C./10 min. extension.

Amplification using primer N7B yielded 3–4 major bands, whereas amplification with N7B did not yield consistent product, suggesting a mismatch at the degenerate third base. To increase specificity and identify the desired amplification product, a 20 ng aliquot of reaction products from the initial PCR using N7B was reamplified using the partially nested gene-specific primer N10 [GAC(T)A(C) GIAAC(T)AAC(T) TTCCCIT(A)C(G)IGA(T)TT, Seq. I.D. No. 3] and vector primer T7 (30 cycles of 94° C./45 sec., 55°/1 min., 72° C./ 2 min. followed by 72° C./10 min. final extension), yielding a 1.7 kb band.

Following identification of the 1.7 kb band as the desired amplification product, the initial PCR reaction was repeated with less (0.9 mM) MgCl$_2$ in the reaction buffer. The resulting 1.7 kb band was then isolated by gel purification (Qiagen) and cloned into EcoRV-digested T-tailed Bluescript II KS vector according to the T/A cloning protocol (Holton and Graham, 1991). Plasmid minipreps from several clones were used for restriction analysis of insert and for primer-directed sequencing of both strands using ABI AmpliTaq dye termination cycle sequencing.

To amplify the 5' end of the CBG cDNA, λZAP-cDNA from the library was again used as a template, this time in conjunction with a T3 vector primer and the gene-specific primer CBG172 (CACATATCTGTGATATTGGTCG, Seq. I.D. No. 4) based on the sequence of the 3' CBG amplification product. A second nested gene-specific primer CBG75 (CCATCTTCTCGGACTGCTC, Seq. I.D. No. 5) was used to re-amplify the former reaction products to confirm the authenticity of the PCR product. The cloning and sequencing of the 5' PCR product was conducted as described above. An exact sequence match in the overlapping regions of the 5' and and 3' end clones confirmed the authenticity of the 5' amplification product.

EXAMPLE 2

Analysis of the CBG cDNA Sequence

The complete CBG cDNA sequence, shown in FIG. 1 and in Seq. I.D. No. 6, is 1909 bp in length. The cDNA includes an open reading frame (Seq. I.D. No. 8) that encodes a 513 amino acid protein (Seq. I.D. No. 7). The 5' and 3'-untranslated regions of the cDNA contain 162 and 187 nucleotides, respectively. The 3'-untranslated region does not contain the conserved eukaryotic polyadenylation signal AAUAAA, as is the case for more than 50% of reported plant mRNA sequences (Wu et al., 1995). Instead, the CBG 3'-untranslated region contains AAUAAA-like sequences like most plant mRNAs (Joshi, 1987).

The 5'-UTR of the CBG cDNA carries a 9 bp AC-rich element (AACCAACAA) that is also present in Arabidopsis PAL1 and bean chalcone synthase (CHS15) genes, and has been proposed to be an elicitor-inducible hypersensitive site (Lawton et al., 1990; Ohl et al., 1990). This indirectly associates CBG with other phenylpropanoid metabolic genes/regulation, and is consistent with the induction of CBG activity in jackpine cell cultures by fungal elicitation (Campbell & Ellis, 1991).

The deduced 513 amino acid protein has a molecular weight of 58.3 kD and a calculated isoelectric point of pH 4.9. The N-terminal amino acid sequence determined for the purified enzyme corresponds to amino acids 24–40 in the deduced sequence. Met35 in the deduced sequence was identified as Thr during N-terminal amino acid sequencing. This mismatch could result from a misidentification during amino acid sequencing, or could represent a polymorphism. The nascent protein contains an N-terminal signal peptide with features characteristic of eukaryotic secretory signal sequences for ER targeting. The "weight matrix" method (von Heijne, 1986) predicts two possible cleavage sites for the signal peptide, one between residues Gly 17 and Phe 18, and a second between Ala23 and Arg24. Since the N-terminal amino acid sequence of the mature protein begins at Arg24, the co-translational processing of the signal peptide appears to occur at the predicted second cleavage site. The protein contains two putative N- asparagine glycosylation sites at Asn223 and Asn447, consistent with the detection of oligosaccharide sidechains in the purified enzyme (Dharmawardhana et al., 1995).

Nucleotide and amino acid sequence homology searches and comparisons were carried out using BLAST (Altschul et al., 1990) on Genbank, EMBL, PDB, SWISS-PROT and PIR databases. Further sequence analysis was performed using PC/GENE or GeneWorks (IntelliGenetics Inc.) software. The derived amino acid sequence of CBG, when compared to other glycohydrolase sequences in the databases, showed the strongest similarity to enzymes belonging to family 1 glycosyl hydrolases (Henrissat, 1991). The β-glucosidases showing the highest similarity (30–50% identity) to CBG were from plant species Prunus, Hordeum, Trifolium, Manihot, Sorghum, Avena, and Costus. The dendrogram in FIG. 2 illustrates that among the plant β-glucosidases, pine CBG is loosely clustered with cyanogenic β-glucosidases from several species (FIG. 2: sequences 7 to 13).

CBG contains several sequence elements that are highly conserved among many family 1 β-glucosidases. Between residues 34 and 48 it carries the N-terminal signature sequence F,X,(FYWM),(GSTA),X,(GSTA),X,(GSTA), (GSTA),(FYN),X,E,X(GSTA) characteristic of family 1 glycosyl hydrolases (Henrissat, 1991). Two of the five cysteine residues found in CBG (Cys 175 and Cys225) are also conserved in these homologous β-glucosidases, suggesting that they may be involved in forming important intramolecular disulfide bridges.

Other conserved sequence elements include the sequence -ENG- at residues 408–410 within the C-terminal signature, and the sequence -NEP- at residues 190–192. These sequence motifs are thought to be important for enzyme activity, and this region may be involved in binding of the pyranose ring during catalysis. The NEP motif of both Bacillus endo-β-1-4-glucanase and CBG is flanked by hydrophobic amino acids; next to the signal peptide, it is the most hydrophobic region of the CBG enzyme. The hydrolytic mechanism of the family 1 β-glucosidases is considered to be general acid catalysis (Sinnott, 1990) with Glu and Asp residues in conserved motifs serving as active site nucleophile and acid catalyst. Evidence from inhibitor and site-directed mutagenesis studies suggests the Glu408 within the conserved ENG motif is the active site nucleophile (Withers et al., 1990; Trimbur et al, 1992). A conserved aspartate residue (Asp427) located 19 residues downstream from the ENG motif of CBG appears to be analogous to Asp374 of Agrobacterium β-glucosidase (cellobiase). This carboxylate side-chain may play the role of acid-base catalyst during hydrolysis of the glycosidic linkage (Trimbur et al., 1992).

EXAMPLE 3

Expression of CBG cDNA in *E. coli*

To express CBG protein in *E. coli*, the full-length coding region for the mature protein (i.e. excluding the signal peptide) was amplified using the 3' end clone (1A6) as the template with the N-terminal primer, NT1 (5' TAGCTAG-CAGGCTGGACAGGAACAACTTC 3', Seq. I.D. No. 9) containing a 5' Nhe1 site, and a C-terminal primer, CT1 (5' CTCGAGACAAGCAGTCTAAATGCT 3', Seq. I.D. No. 10) containing a Xho 1 site. The resulting 1.5 kb DNA fragment was ligated into Bluescript II KS by T/A cloning as described above. The structure of the junctions of this construct was confirmed by sequencing and it was then inserted as a Nhe1/Xho1 fragment into expression vector pET21a (Novagen). Because, the Nhe1 site was used to introduce the cDNA into the pET vector, three non-CBG amino acids (Met, Ala, Ser) were added to the N-terminus of the expressed protein. To avoid the expression of the vector His-tag at the 3' end, the native stop codon of CBG was included. The expressed protein was thus identical in sequence to the mature CBG expressed in planta, except for the additional tripeptide at the N-terminus. Following transformation into *E.coli* strain DH5α and verification of the plasmid integrity by restriction digestion, it was introduced into the expression host BL21 (DE3).

To express CBG, the bacteria were grown to log phase ($A_{600}$=0.6–0.9) followed by an additional 2–3 h incubation at 29–37° C. in the presence or absence of 0.4–1 mM IPTG. The expressed CBG in the soluble protein fraction was purified by preparative Q-Sepharose chromatography followed by QMA-Memsep (Millipore) chromatography.

As noted above, the functional characteristic of the CBG enzyme is its ability to hydrolyze coniferin. This activity can be measured using the simple β-glucosidase assay described by Dharwardhana et al. (1995), conducted as follows: enzyme preparations (10–50 μl) and glucoside substrate (coniferin) (2 mM final concentration) in 0.2M MES, pH 5.5 buffer in a final volume of 150 μl are incubated at 30° C. for 30 min. The reaction is stopped by basification of the assay mixture with an equal volume of 0.5M CAPS buffer (Sigma Chemical Co., St. Louis, Mo., pH 10.5 and the activity measured by determining the absorbance of the released aglycone. The activity of the enzyme can be measured not only against coniferin, but also against related glucosides including 4-NPG, 2-NPG, MUG and the synthetic coniferin analog VRA-G. For quantitative calculations, the following analysis wavelengths and values ($mM^{-1} \times cm^{-1}$) were used: coniferyl alcohol, 325 nm, $\epsilon$=7.0; sinapyl alcohol, 315 nm, $\epsilon$=11.2; 2-nitrophenol, 420 nm, $\epsilon$=4.55, 4-nitrophenol, 400 nm, $\epsilon$=19.3; 4-methyl umbelliferone, 360 nm, $\epsilon$=18.25; VRA-G, 490 nm, $\epsilon$=38.6; salicyl alcohol, 295 nm, $\epsilon$=3.3.

Soluble proteins and insoluble proteins (inclusion bodies) prepared from induced and uninduced bacterial cells were assayed for coniferin hydrolysis activity by the method described above. Only the soluble protein fraction of induced cells displayed this activity. The activity in this fraction could be increased up to 2-fold by increasing the IPTG concentration from 0.4 –1.0 mM, and by reducing the growing temperature from 37° C. to 29° C. Activity staining of nondenaturing PAGE gels using the chromogenic coniferin analogue VRA-G revealed a β-glucosidase-active protein band in induced cell extracts. This protein was purified by anion exchange chromatography using coniferin as the substrate for monitoring β-glucosidase activity. The purified enzyme often migrated as a doublet on nondenaturing gels. Both protein bands in the doublet showed β-glucosidase activity, as assayed by hydrolysis of VRA-G. This could be due to partial degradation, alternate forms of folding, or the synthesis of a truncated protein at the 5' end where CBG has a prokaryotic ribosome binding Shine-Dalgarno sequence (GAAGGAG). The latter would result in the synthesis of a polypeptide that is truncated at the N-terminus, as opposed to the full-length polypeptide initiated by ribosome binding to the standard ribosome binding site in the vector. As shown in Table 1 below, the CBG expressed in *E. coli* and the enzyme purified from the pine xylem showed almost identical substrate specificities.

TABLE 1

Substrate specificity of coniferin β-glucosidase purified from pine xylem and *E. coli*- expressed CBG-cDNA. 100% activity represents 14pKat for native coniferin beta-glucosidase and 22pKat for the recombinant enzyme.

| Substrate | Relative activity | |
|---|---|---|
| | Native CBG | *E. coli* CBG |
| coniferin | 100 | 100 |
| syringin | 51 | 65 |
| 4-methyl umbelliferyl-β-glucoside | 18 | 20 |
| 2-nitrophenyl-β-glucoside | 51 | 50 |
| 4-nitrophenyl-β-glucoside | 30 | 35 |

EXAMPLE 4

Preferred Method for Making the CBG cDNA

With the provision of the CBG cDNA sequence shown in Seq. I.D. No. 6, the polymerase chain reaction (PCR) may now be utilized in a preferred method for producing the CBG cDNA. PCR amplification of the CBG cDNA sequence may be accomplished either by direct PCR from an appropriate cDNA library or by Reverse-Transcription PCR (RT-PCR) using RNA extracted from plant cells as a template. Methods and conditions for both direct PCR and RT-PCR are known in the art and are described in Innis et al. (1990). Suitable plant cDNA libraries for direct PCR include the *Pinus contorta* library as described above. Other plant cDNA libraries may be used in order to amplify orthologous cDNAs of other species; for example, the Arabidopsis cDNA library described by Newman et al. (1994) may be used to amplify the Arabidopsis ortholog.

The selection of PCR primers will be made according to the portions of the cDNA which are to be amplified. Primers may be chosen to amplify small segments of the cDNA or the entire cDNA molecule. Variations in amplification conditions may be required to accommodate primers of differing lengths; such considerations are well known in the art and are discussed in Innis et al. (1990), Sambrook et al. (1989), and Ausubel et al (1992). By way of example only, the entire CBG cDNA molecule as shown in Seq. I.D. No. 6 may be amplified using the following combination of primers:
5' GGATTTGGACCTGAAAATATCAAT 3' (Seq. I.D. No. 11)
5' CAATGTTCTTACCCTGCAGTTCCC 3' (Seq. I.D. No. 12)
The open reading frame portion of the cDNA may be amplified using the following primer pair:
5' ATGGAGGTGTCTGTGTTGATGTGGGTA 3' (Seq. I.D. No. 13)
5' AATGCTGCTGCTGCTTCTAATACTTCC 3' (Seq. I.D. No. 14)
These primers are illustrative only; it will be appreciated by one skilled in the art that many different primers may be derived from the provided cDNA sequence in order to amplify particular regions of this cDNA. Suitable amplification conditions include those described above for the original isolation of the CBG cDNA. As is well known in the art, amplification conditions may need be varied in order to amplify orthologous genes where the sequence identity is not 100%; in such cases, the use of nested primers, as described above may be beneficial. Resequencing of PCR products obtained by these amplification procedures is recommended; this will facilitate confirmation of the CBG cDNA sequence and will also provide information on natural variation on this sequence in different ecotypes, cultivars and plant populations.

Oligonucleotides which are derived from the CBG cDNA sequence and which are suitable for use as PCR primers to amplify the CBG cDNA are encompassed within the scope of the present invention. Preferably, such oligonucleotide primers will comprise a sequence of 15–20 consecutive nucleotides of the CBG cDNA. To enhance amplification specificity, primers of 20–30 nucleotides or more in length may also be used.

EXAMPLE 5

Use of the CBG CDNA to Produce Plants with Modified Lignin Content

Once a gene (or cDNA) encoding a protein involved in the determination of a particular plant characteristic has been isolated, standard techniques may be used to express the cDNA in transgenic plants in order to modify that particular plant characteristic. The basic approach is to clone the cDNA into a transformation vector, such that it is operably linked to control sequences (e.g., a promoter) which direct expression of the cDNA in plant cells. The transformation vector is then introduced into plant cells by one of a number of techniques (e.g., electroporation) and progeny plants containing the introduced cDNA are selected. Preferably all or part of the transformation vector will stably integrate into the genome of the plant cell. That part of the transformation vector which integrates into the plant cell and which contains the introduced cDNA and associated sequences for controlling expression (the introduced "transgene") may be referred to as the recombinant expression cassette.

Selection of progeny plants containing the introduced transgene may be made based upon the detection of an altered phenotype. Such a phenotype may result directly from the cDNA cloned into the transformation vector or may be manifested as enhanced resistance to a chemical agent (such as an antibiotic) as a result of the inclusion of a dominant selectable marker gene incorporated into the transformation vector.

The choice of (a) control sequences and (b) how the cDNA (or selected portions of the cDNA) are arranged in the transformation vector relative to the control sequences determine, in part, how the plant characteristic affected by the introduced cDNA is modified. For example, the control sequences may be tissue specific, such that the cDNA is only expressed in particular tissues of the plant (e.g., vascular systems) and so the affected characteristic will be modified only in those tissues. The cDNA sequence may be arranged relative to the control sequence such that the cDNA transcript is expressed normally, or in an antisense orientation. Expression of an antisense RNA that is the reverse complement of the cloned cDNA will result in a reduction of the targeted gene product (the targeted gene product being the protein encoded by the plant gene from which the introduced cDNA was derived). Over-expression of the introduced cDNA, resulting from a plus-sense orientation of the cDNA relative to the control sequences in the vector, may lead to an increase in the level of the gene product, or may result in a reduction in the level of the gene product due to co-suppression (also termed "sense suppression") of that gene product.

Successful examples of the modification of plant characteristics by transformation with cloned cDNA sequences are replete in the technical and scientific literature. Selected examples, which serve to illustrate the level knowledge in this field of technology include:

U.S. Pat. No. 5,451,514 to Boudet (modification of lignin synthesis using antisense RNA and co-suppression);

U.S. Pat. No. 5,443,974 to Hitz (modification of saturated and unsaturated fatty acid levels using antisense RNA and co-suppression);

U.S. Pat. No. 5,530,192 to Murase (modification of amino acid and fatty acid composition using antisense RNA);

U.S. Pat. No. 5,455,167 to Voelker (modification of medium chain fatty acids)

U.S. Pat. No. 5,231,020 to Jorgensen (modification of flavonoids using co-suppression); and U.S. Pat. No. 5,583,021 to Dougherty (modification of virus resistance by expression of plus-sense RNA)

These examples include descriptions of transformation vector selection, transformation techniques and the construction of constructs designed to over-express the introduced cDNA, untranslatable RNA forms or antisense RNA. In light of the foregoing and the provision herein of the CBG cDNA, it is thus apparent that one of skill in the art will be able to introduce this cDNA, or derivative forms of the cDNA (e.g., antisense forms), into plants in order to produce plants having modified lignin content. Example 6 below provides an exemplary illustration of how an antisense form of the CBG cDNA may be introduced into conifers using ballistic transformation, in order to produce conifers having altered lignin content.

a. Plant Types

Lignins are found in all plant types, and thus DNA molecules according to the present invention (e.g., the CBG cDNA, homologs of the CBG cDNA and antisense forms) may be introduced into any plant type in order to modify the lignin composition of the plant. Thus, the sequences of the present invention may be used to modify lignin composition in any higher plants including monocotyledonous plants such as lily, corn, rice, wheat and barley as well as dicotyledonous plants, such as tomato, potato, soy bean, cotton, tobacco, sunflower, safflower and brasicca. As noted above, the present invention is expected to be particularly useful in woody species such as species belonging to the genera Picea, Pseudotsuga, Tsuga, Sequoia, Abies, Thuja, Libocedrus, Chamaecyparis and Laryx. Pines are expected to be a particularly suitable choice for genetic modification by the methods disclosed herein, including lodgepole pine (*Pinus contorta*), the species from which the CBG cDNA was cloned.

b. Vector Construction, Choice of Promoters

A number of recombinant vectors suitable for stable transfection of plant cells or for the establishment of transgenic plants have been described including those described in Pouwels et al., (1987), Weissbach and Weissbach, (1989), and Gelvin et al., (1990). Typically, plant transformation vectors include one or more cloned plant genes (or cDNAs) under the transcriptional control of 5' and 3' regulatory sequences and a dominant selectable marker. Such plant transformation vectors typically also contain a promoter regulatory region (e.g., a regulatory region controlling inducible or constitutive, environmentally-or developmentally-regulated, or cell- or tissue-specific expression), a transcription initiation start site, a ribosome binding site, an RNA processing signal, a transcription termination site, and/or a polyadenylation signal.

Examples of constitutive plant promoters which may be useful for expressing the CBG cDNA include: the cauliflower mosaic virus (CaMV) 35S promoter, which confers constitutive, high-level expression in most plant tissues (see, e.g., Odel et al., 1985; Dekeyser et al., 1990; Terada and Shimamoto, 1990); the nopaline synthase promoter (An et al., 1988); and the octopine synthase promoter (Fromm et al., 1989).

A variety of plant gene promoters that are regulated in response to environmental, hormonal, chemical, and/or developmental signals, also can be used for expression of the CBG cDNA in plant cells, including promoters regulated by: (a) heat (Callis et al., 1988); (b) light (e.g., the pea rbcS-3A promoter, Kuhlemeier et al., 1989, the maize rbcS promoter, Schaffner and Sheen, 1991, and the chlorophyll a/b-binding protein promoter); (c) hormones, such as abscisic acid (Marcotte et al., 1989); (d) wounding (e.g., wunI, Siebertz et al., 1989); and (e) chemicals such as methyl jasminate or salicylic acid. It may also be advantageous to employ tissue-specific promoters, such as those described by Roshal et al., (1987), Schernthaner et al., (1988), and Bustos et al., (1989).

Plant transformation vectors may also include RNA processing signals, for example, introns, which may be positioned upstream or downstream of the CBG cDNA sequence in the transgene. In addition, the expression vectors may also include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Finally, as noted above, plant transformation vectors may also include dominant selectable marker genes to allow for the ready selection of transformants. Such genes include those encoding antibiotic resistance genes (e.g., resistance to hygromycin, kanamycin, bleomycin, G418, streptomycin or spectinomycin) and herbicide resistance genes (e.g., phosphinothricin acetyltransferase).

C. Arrangement of CBG cDNA in Vector

As noted above, the particular arrangement of the CBG cDNA in the transformation vector will be selected according to the expression of the cDNA desired.

Sense Expression

Where enhanced lignin synthesis is desired, the CBG cDNA may be operably linked to a constitutive high-level promoter such as the CaMV 35S promoter. As noted below, modification of lignin synthesis may also be achieved by introducing into a plant a transformation vector containing a variant form of the CBG cDNA, for example a form which varies from the exact nucleotide sequence of the CBG cDNA, but which encodes a protein that retains the functional characteristic of the CBG protein, i.e. coniferin hydrolysis activity.

Sense Suppression

Constructs in which the CBG cDNA (or variants thereon) are over-expressed may also be used to obtain co-suppression of the endogenous CBG gene in the manner described in U.S. Pat. No. 5,231,021 to Jorgensen. Such co-suppression (also termed sense suppression) does not require that the entire CBG cDNA be introduced into the plant cells, nor does it require that the introduced sequence be exactly identical to the CBG cDNA. However, as with antisense suppression, the suppressive efficiency will be enhanced as (1) the introduced sequence is lengthened and (2) the sequence similarity between the introduced sequence and the endogenous CBG geneis increased. Sense-suppression is believed to be modulated, in part, by the position on the plant genome into which the introduced sequence integrates.

Antisense Expression

In contrast, a reduction of lignin synthesis may be obtained by introducing antisense constructs based on the CBG cDNA sequence into plants. For antisense suppression, the CBG EDNA is arranged in reverse orientation relative to the promoter sequence in the transformation vector. The introduced sequence need not be the full length CBG cDNA, and need not be exactly homologous to the CBG cDNA. Generally, however, where the introduced sequence is of shorter length, a higher degree of homology to the native CBG sequence will be needed for effective antisense suppression. Preferably, the introduced antisense sequence in the vector will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous CBG gene in the plant cell. Although the exact mechanism by which antisense RNA molecules interfere with gene expression has not been elucidated, it is believed that antisense RNA molecules bind to the endogenous MRNA molecules and thereby inhibit translation of the endogenous mRNA.

Suppression of endogenous CBG gene expression can also be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haseloff. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Untranslatable RNA

Suppression of native gene expression may be achieved by transforming the plant with a sequence that is homologous to the target gene, but which is rendered untranslatable by a genetic modification such as the introduction of a premature stop codon. This approach is described in U.S. Pat. No. 5,583,021. The introduced CBG sequence is preferably 50–100 nucleotides in length, although longer sequences, such as 100–250 nucleotides are preferred. The introduced sequence is engineered to encode an untranslatable RNA; the introduction of a premature stop codon early on in the coding region is a preferred way of achieving this. The sequence need not be perfectly homologous to the target CBG sequence, but at least 80%, and preferably 85% sequence homology will likely be more effective than lower homologies.

d. Transformation and Regeneration Techniques

Transformation and regeneration of both monocotyledonous and dicotyledonous plant cells are now routine, and the selection of the most appropriate transformation and regeneration techniques will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene mediated transformation; transformation using viruses; micro-injection of plant cells; micro-projectile bombardment of plant cells; vacuum infiltration; and *Agrobacterium tumeficiens* (AT) mediated transformation. Typical procedures for transforming and regenerating plants are described in the patent documents listed at the beginning of this section. In addition, methods for transforming woody species are described in Ellis et al. (1993), Ellis et al. (1996), U.S. Pat. No. 5,122,466, "Ballistic Transformation of Conifer" and U.S. Pat. No. 4,795,855, "Transformation and Foreign Gene Expression with Woody Species".

e. Selection of Transformed Plants

Following transformation and regeneration of plants with the transformation vector, transformed plants are preferably selected using a dominant selectable marker incorporated into the transformation vector. Typically, such a marker will confer antibiotic resistance on the seedlings of transformed plants, and selection of transformants can be accomplished by exposing the seedlings to appropriate concentrations of the antibiotic.

After transformed plants are selected and grown to maturity, they can be assayed to determine whether coniferin beta-glucosidase synthesis has been altered as a result of the introduced transgene. This can be done in several ways, including by extracting and quantifying the enzyme activity as described in Example 6. In addition, lignification may be determined histochemically, and lignin content may be quantified, as described in Example 6. Also, antisense or sense suppression of the endogenous CBG gene may be detected by analyzing mRNA expression on Northern blots.

EXAMPLE 6

Introduction Of Antisense CBG cDNA Sequence Into White Spruce (Picea Glauca)

Figure 3:
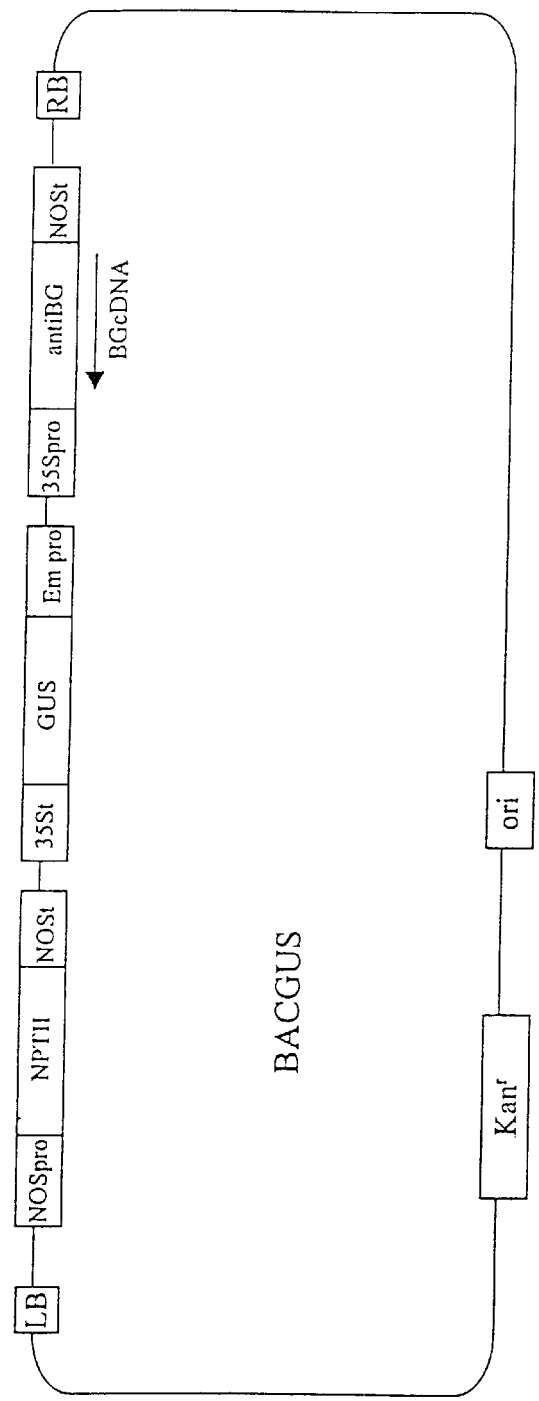
FIG. 3 shows a transformation vector suitable for introducing antisense CBG into plants.

By way of example, the following methodology may be used to produce white spruce trees having an altered lignin content. The CBG cDNA is operably linked, but in reverse orientation, to the enhanced cauliflower mosaic virus (CaMV) 35S promoter in place of the BT gene in plasmid pTVBT41100 (Ellis et al., 1993). (Many other plants tranaformation vectors have been described and would be suitable for introducing CBG-based constructs into plants. Vector pBACGGUS shown in FIG. 3 is one such alternative vector that may be used). Somatic embryos of *Picea glauca* are differentiated from embryogenic white spruce callus line and cultured as described by Ellis et al. (1993). Plasmid DNA is adhered to 1–3 M gold particles (0.5 g DNA /mg gold) by calcium chloride and spermidine precipitation. Gold particles containing the DNA are then loaded on to carrier sheets at a rate of 0.05 mg/cm$^2$ and these particles are then introduced into somatic embryos as described by Ellis et al. (1991). Transformed embryos are selected using kanamycin. Regeneration of transgenic plants (via the production of embryogenic callus) is achieved using the culture conditions described by Ellis et al. (1993).

In order to determine coniferin beta-glucosidase activity in the transgenic plants, the enzyme is extracted as described in Example 1 above, and the activity is assayed using the β-glucosidase assay described in Example 3 above. Plants transformed with the same vector without the CBG cDNA insert should preferably be used as controls. In situ localization of the enzyme activity can be determined using VRA-G as described by Dharmawardhana et al. (1995). Lignin in the stem sections is detected histochemically by Basic Fuchsin-induced fluorescence and imaging on a confocal laser scanning microscope as described by Dharmawardhana et al. (1992). In order to determine the effect of introducing the antisense construct into the plant on lignin content, standard methods are used to quantify lignin in the transformed plant (and control plants). Standard methods of quantifying lignin include the thioglycolic acid procedure as described by Whitmore (1978) and the acetyl bromide procedure as described by Liyama and Wallis (1990).

EXAMPLE 7

CBG Genes in Other Plant Species

Orthologs of the CBG gene may be isolated from a number of plant species, particularly woody species such as plants from the genera Picea, Pseudotsuga, Tsuga, Sequoia, Abies, Thuja, Libocedrus, Chamaecyparis and Laryx. With the provision herein of the prototypical CBG protein from Pinus and the cDNA sequence that encodes this protein, the cloning by standard methods of cDNAs and genes that encode CBG protein orthologs in other plant species is now enabled. As described above, orthologs of the disclosed Pinus CBG protein have CBG protein biological activity and are typically characterized by possession of at least 50% sequence identity counted over the full length alignment with the amino acid sequence of Pinus CBG using the NCBI Blast 2.0, gapped blastp set to default parameters. Proteins with even greater similarity to the reference sequences will show increasing percentage identities when assessed by this method, such as at least 60%, at least 65%, at least 70%, at least 75%, at least 80%, at least 90% or at least 95% sequence identity.

Both conventional hybridization and PCR amplification procedures may be utilized to clone sequences encoding CBG protein orthologs. Common to both of these techniques is the hybridization of probes or primers derived from the Pinus CBG cDNA sequence to a target nucleotide preparation, which may be, in the case of conventional hybridization approaches, a cDNA or genomic library or, in the case of PCR amplification, a cDNA or genomic library, or an mRNA preparation.

Direct PCR-amplification may be performed on cDNA or genomic libraries prepared from the plant species in question, or RT-PCR may be performed using MRNA extracted from the plant cells using standard methods. PCR primers will comprise at least 15 consecutive nucleotides of the Pinus CBG cDNA. One of skill in the art will appreciate that sequence differences between the Pinus CBG cDNA or gene and the target nucleic acid to be amplified may result in lower amplification efficiencies. To compensate for this, longer PCR primers or lower annealing temperatures may be used during the amplification cycle. Where lower annealing temperatures are used, sequential rounds of amplification using nested primer pairs may be necessary to enhance specificity.

For conventional hybridization techniques the hybridization probe is preferably conjugated with a detectable label such as a radioactive label, and the probe is preferably of at least 20 nucleotides in length. As is well known in the art, increasing the length of hybridization probes tends to give enhanced specificity. The labeled probe derived from the Pinus cDNA sequence may be hybridized to a plant cDNA or genomic library and the hybridization signal detected using means known in the art. The hybridizing colony or plaque (depending on the type of library used) is then purified and the cloned sequence contained in that colony or plaque isolated and characterized.

Homologs and orthologs of the Pinus CBG cDNA sequence include molecules that hybridize under stringent conditions to the disclosed prototypical CBG cDNA, or fragments thereof. Stringent hybridization conditions are hybridization at 65° C. in 6×SSC, 5×Denhardt's solution, 0.5% SDS and 100 μg sheared salmon testes DNA, followed by 15–30 minute sequential washes at 65° C. in 2×SSC, 0.1% SDS, followed by 1×SSC, 0.1% SDS and finally 0.2×SSC, 0.1% SDS. Lower stringency hybridization conditions (to detect less closely related homologs) are performed as described above but at 50° C. (both hybridization and wash conditions); however, depending on the strength of the detected signal, the wash steps may be terminated after the first 2×SSC, 0.1% SDS wash.

Orthologs of the Pinus CBG may alternatively be obtained by immunoscreening of an expression library. With the provision herein of the disclosed Pinus CBG nucleic acid sequences, the enzyme may be expressed and purified in a heterologous expression system (e.g., *E coli*) and used to raise antibodies (monoclonal or polyclonal) specific for the Pinus CBG protein. Antibodies may also be raised against synthetic peptides derived from the Pinus CBG amino acid sequence presented herein. Methods of raising antibodies are well known in the art and are described in Harlow and Lane (1988). Such antibodies can then be used to screen an expression cDNA library produced from the plant from which it is desired to clone the CBG ortholog, using routine methods. The selected cDNAs can be confirmed by sequencing and enzyme activity.

EXAMPLE 8

CBG Sequence Variants

With the provision of the Pinus CBG protein and CBG cDNA sequences herein, the creation of variants of these sequences is now enabled. Variant CBG proteins include proteins that differ in amino acid sequence from the Pinus CBG sequence disclosed but which retain CBG protein biological activity. Such proteins may be produced by manipulating the nucleotide sequence of the Pinus CBG cDNA using standard procedures such as site-directed mutagenesis or the polymerase chain reaction. The simplest modifications involve the substitution of one or more amino acids for amino acids having similar biochemical properties. These so-called conservative substitutions are likely to have minimal impact on the activity of the resultant protein. Table 2 shows amino acids which may be substituted for an original amino acid in a protein and which are regarded as conservative substitutions.

TABLE 2

| Original Residue | Conservative Substitutions |
| --- | --- |
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |

TABLE 2-continued

| Original Residue | Conservative Substitutions |
| --- | --- |
| Tyr | trp; phe |
| Val | ile; leu |

More substantial changes in enzymatic function or other features may be obtained by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine. The effects of these amino acid substitutions or deletions or additions may be assessed for CBG protein derivatives by analyzing the ability of the derivative proteins to hydrolyze coniferin in the assay described.

Variant CBG cDNA or genes may be produced by standard DNA mutagenesis techniques, for example, M13 primer mutagenesis. Details of these techniques are provided in Sambrook et al. (1989), Ch. 15. By the use of such techniques, variants may be created which differ in minor ways from the Pinus CBG cDNA sequences disclosed, yet which still encode a protein having CBG protein biological activity. DNA molecules and nucleotide sequences which are derivatives of those specifically disclosed herein and which differ from those disclosed by the deletion, addition or substitution of nucleotides while still encoding a protein that has CBG protein biological activity are comprehended by this invention. In their simplest form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence in such a way that, while the nucleotide sequence is substantially altered, it nevertheless encodes a protein having an amino acid sequence identical or substantially similar to the disclosed Pinus CBG protein sequence. For example, the 23rd amino acid residue of the Pinus CBG protein is alanine. This is encoded in the Pinus CBG open reading frame (ORF) by the nucleotide codon triplet GCT. Because of the degeneracy of the genetic code, three other nucleotide codon triplets—GCA, GCC and GCG—also code for alanine. Thus, the nucleotide sequence of the Pinus CBG ORF could be changed at this position to any of these three codons without affecting the amino acid composition of the encoded protein or the characteristics of the protein. Based upon the degeneracy of the genetic code, variant DNA molecules may be derived from the cDNA sequence disclosed herein using standard DNA mutagenesis techniques as described above, or by synthesis of DNA sequences. Thus, this invention also encompasses nucleic acid sequences which encode a CBG protein but which vary from the disclosed nucleic acid sequences by virtue of the degeneracy of the genetic code.

Variants of the CBG protein may also be defined in terms of their sequence identity with the prototype CBG protein shown in Seq. I.D. No. 7. As described above, CBG proteins have CBG biological activity and share at least 60% sequence identity with the Pinus CBG protein. Nucleic acid sequences that encode such proteins may readily be determined simply by applying the genetic code to the amino acid sequence of a CBG protein, and such nucleic acid molecules may readily be produced by assembling oligonucleotides corresponding to portions of the sequence.

The Pinus CBG gene or cDNA, and orthologs of these sequences from other plants, may be incorporated into transformation vectors and introduced into plants to produce plants having modified lignin content, as described above.

REFERENCES

Altschul & Gish. (1996). *Methods Enzymol.*, 266: 460–80.
Altschul et al. (1990). *J. Mol. Biol.*, 215,403–10
Altschul et al. (1990). *J. Mol. Biol.* 215: 403–410
An et al. (1988) *Plant Physiol.* 88: 547
Ausubel et al. (1987). In *Current Protocols in Molecular Biology*, Greene Publishing Associates and Wiley-Intersciences.
Baird et al. (1990) *Biochem. Biophy. Res. Comm.* 169: 1035–1039
Bolton and McCarthy (1962) *Proc. Natl. Acad. Sci. USA* 48: 1390.
Bonner et al. (1973). *J. Mol. Biol.* 81: 123.
Brzoboha et al. (1993) *Science* 262: 1051
Bustos et al. (1989) *Plant Cell* 1: 839
Callis et al. (1988) *Plant Physiol.* 88: 965
Campbell & Ellis (1991) *Planta* 180: 409–417
Castle et al..(1992) *J. Bacteriol* 174, 1478–1486
Christou (1996) *Trends Plant Sci.* 1, 423–431
Corpet et al. (1988). *Nucleic Acids Research* 16, 10881–90.
Dekeyser et al. (1990) *Plant Cell* 2: 591
Dharmawardhana et al. (1992) *Can. J. Bot.* 70: 2238–2244
Dharmawardhana et al. (1995) *Plant Physiol.* 107: 331–339
Elkind et al. (1990) *Proc Nat Acad Sci USA* 87: 9057–9061
Ellis et al. (1991) *Plant. Mol. Biol.* 17: 19–27
Ellis et al. (1993) *Bio/Technology* 11: 84–89
Ellis et al. (1996) In *Somatic Cell Genetics and Molecular Genetics of Trees*, Boerjan and Ahuja (Eds.), Kluwer Academic Publishers, The Netherlands
Falk et al. (1992) *Plant Sci.* 83, 181–186
Fan and Conn (1985) *Arch Biochem Biophys* 243: 361–373
Freudenberg & Harkin (1963) *Phytochemistry* 2: 189–193
Fromm et al. (1989) *Plant Cell* 1: 977
Fukushima & Terashima (1990) *J Wood Chem. Technol.* 10, 413–433
Fukushima & Terashima (1991) *Holzforschung.* 45, 87–89
Gelvin et al. (1990) *Plant Molecular Biology Manual*, Kluwer Academic Publishers.
Harkin and Obst (1973) *Science* 180: 296–297
Harlow & Lane (1988) *Antibodies: A Laboratory Manual*, Cold Spring Harbor Laboratory, New York.
Henrissat (1991) *Biochem. J.*, 280: 309–316
Higgins and Sharp (1988). *Gene*, 73: 237–244.
Higgins and Sharp (1989). *CABIOS*: 151–153.
Holton & Graham (1991) *Nucl. Acids Res.* 191: 1156–1158
Hosel and Todenhagen (1980) *Phytochemistry* 19: 1349–1353
Hosel et al. (1982) *Plant Cell Orgn Cult* 1: 137–148
Hosel et al. (1987) *Arch Biochem Biophys* 252: 152–162

Hrazdina & Jensen (1992) *Annu. Rev. Plant Physiol. Plant Mol. Biol.* 43: 241–267

Hrazdina & Wagner (1985) *Arch. Biochem. Biophys.* 237: 88–100.

Huang, et al. (1992). *Computer Applications in the Biosciences* 8, 155–65.

Hughes & Dunn (1982) *Plant Mol. Biol.* 1: 169–181.

Innis et al. (1990). *PCR Protocols, A Guide to Methods and Applications*, Innis et al. (eds.), Academic Press, Inc., San Diego, Calif.

Jefferson et al. (1981) *EMBO Journal* 6: 3901

Joshi (1987) *Nuc. Acids Res.* 15: 9627–9640

Klein et al. (1985) *Biochem. et Biophys. Acta.* 815: 468–476

Kuhlemeier et al. (1989) *Plant Cell* 1: 471

Laemmli (1970) *Nature* 277: 680–6851

Lawton et al. (1990) *Plant Cell Rep.* 8: 561–564

Leah et al. (1995) *J. BioL Chem.* 270: 15789–15796

Lee and Douglas (1994) *Plant Physiol suppl* 105: 37

Leinhos & Savidge (1993) *Can J. For. Res.* 23: 343–348

Leinhos et al. (1994) *Phytochemistry* 37: 311–315

Lewinsohn et al. (1994) *Plant Mol. Biol. Rep.* 12: 20–25

Li et al. (1992) *Plant Physiol* 100: 282–290

Liyama & Wallis (1990) *J. Sci. Food Agriculture* 51: 145–161

Marcinowski and Grisebach (1978) *Eur J. Biochem* 87: 37–44

Marcotte et al. (1989) *Plant Cell* 1: 969

Muckerheide et al. (1987) *J. Immunol* 138: 833–837

Needleman and Wunsch (1970). *J. Mol Biol.* 48: 443.

Newman et al. (1994) *Plant Physiol.* 106: 1241–1255

Odel et al. (1985) *Nature* 313: 810.

Ohl et al. (1990) *Plant Cell* 2, 837–848

Oxtoby et al. (1991) *Plant Mol. Biol.* 17, 209–219.

Pearson and Lipman (1988) *Proc Nat Acad Sci USA* 85: 2444–2448

Pearson et al. (1994). *Methods in Molecular Biology* 24, 307–31.

Pickett-Heaps (1968) *Protoplasma* 65: 181–190

Pouwels et al. (1987) *Cloning Vectors: A Laboratory Manual*, 1985, supp.

Roshal et al. (1987) *EMBO J.* 6: 1155.

Sambrook et al. (1989) Molecular cloning: A laboratory manual. Cold Spring Harbor Laboratory, Cold Spring Harbor, N.Y.

Savidge (1988) *Can. J. Bot.* 66: 2099–2012

Savidge (1989) *Can J. Bot* 67: 2663–2668

Schaffner and Sheen (1991) *Plant Cell* 3: 997

Schernthaner et al. (1988) *EMBO J.* 7: 1249.

Schuch (1993) *Phytochem Soc North Am* 33 (1): 19

Siebertz et al. (1989) *Plant Cell* 1: 961

Simos et al. (1994) *Biochimica et Biophysica Acta* 1199: 52–58

Sinnott (1990) *Chem. Rev.* 90: 1171–1202

Smith and Waterman (1981). *Adv. Appl. Math.* 2: 482.

Southern (1975) *J. Mol. Biol.* 98: 503.

Takabe et al. (1989) in *Plant Cell Wall Polymers, Biogenesis & Biodegradation*, Lewis N. G. & Paice M. G. (eds.) ACS Symp. Ser. 399. Amer. Chem. Soc. Washington D.C. pp. 47–66

Terada and Shimamoto (1990) *Mol. Gen. Genet.* 220: 389

Terashima & Fukushima (1988) *Wood Sci. Technol.* 22, 259–270

Terashima et al. (1986) *J. Wood Sci. Technol.* 6: 495–504

Terazawa et al. (1984) *Mokuzai Gakkaishi* 30: 322–328

Trimbur et al.(1992) *J. Biol. Chem.* 267: 10248–10251 van-Uden et al. (1991) *Planta* 183: 25–30

Varghese et al. (1994) *Proc. Natl. Acad. Sci USA* 91: 2785–2789 von Heijne (1986) *Nucl Acids Res.* 14: 4683–4690

Wagner et al. (1987) *Proc. Natl. Acad. Sci. USA.* 84: 2097–2100

Weissbach and Weissbach (1989) *Methods for Plant Molecular Biology*, Academic Press.

Whetten & Sederoff (1995) *Plant Cell* 7: 1001–1013

Whitmore (1978) *Phytochemistry* 17: 412–425

Withers et al. (1990) *J. Amer. Chem. Soc.* 112: 5887–5889

Wu et al. (1995) *Plant J.* 8: 323–329

Xue et al. (1992) *Plant Mol. Biol.* 18: 387–398

Yeoh and Woo (1992) *Phytochemistry* 31: 2263–2265

---

We claim:

1. An isolated nucleic acid molecule encoding a protein comprising the amino acid sequence shown in Seq. I.D. No. 7.

2. An isolated nucleic acid molecule according to claim 1 wherein the molecule comprises a sequence selected from the group consisting of:
   (a) Seq. I.D. No. 6; and
   (b) Seq. I.D. No. 8.

3. A recombinant nucleic acid molecule comprising a promoter sequence operably linked to a nucleic acid sequence according to claims 1.

4. A microbial or plant cell transformed with a recombinant nucleic acid molecule according to claim 3.

5. A transgenic plant comprising a recombinant nucleic acid molecule according to claim 3.

6. A transgenic plant according to claim 5 wherein the plant is a conifer.

7. A transgenic plant according to claim 6 wherein the plant is a Pinus species.

8. An isolated nucleic acid molecule comprising:
   at least 20 contiguous nucleotides of the sequence shown in Seq. I.D. No. 6.

9. A recombinant nucleic acid molecule comprising a promoter sequence operably linked to a nucleic acid sequence according to claim 8, wherein the nucleic acid molecule is operably linked to the promoter sequence in sense or antisense orientation.

10. A microbial or plant cell transformed with a recombinant nucleic acid molecule according to claim 9.

11. A transgenic plant comprising a recombinant nucleic acid molecule according to claim 9.

12. A transgenic plant according to claim 11 wherein the plant is a conifer.

13. A transgenic plant according to claim 11 wherein the plant is a Pinus species.

14. An isolated nucleic acid molecule that:
   (a) hybridizes with the nucleic acid sequence shown in Seq. I.D. No. 8 under wash conditions of 65° C., 0.2×SSC and 0.1% SDS; and
   (b) encodes a protein having coniferin beta-glucosidase biological activity.

15. A recombinant nucleic acid molecule comprising a promoter sequence operably linked to a nucleic acid sequence according to claim 14.

16. A microbial or plant cell transformed with a recombinant nucleic acid molecule according to claim 15.

17. A transgenic plant comprising a recombinant nucleic acid molecule according to claim 15.

18. A transgenic plant according to claim 17 wherein the plant is a conifer.

19. A transgenic plant according to claim 17 wherein the plant is a Pinus species.

20. A recombinant nucleic acid molecule comprising a promoter sequence operably linked to a nucleic acid sequence selected from the group consisting of:
  (a) a nucleic acid sequence encoding an untranslatable plus-sense transcript that hybridizes with the nucleic acid sequence shown in Seq. I.D. No. 8 under wash conditions of 65° C., 0.2×SSC and 0.1% SDS, wherein the transcript is in sense orientation relative to the promoter sequence; and
  (b) a sequence that hybridizes with the nucleic acid sequence shown in Seq. I.D. No. 8 under wash conditions of 65° C., 0.2×SSC and 0.1 % SDS, wherein the sequence is in antisense orientation relative to the promoter sequence.

21. A transgenic plant comprising a recombinant nucleic acid molecule according to claim 20.

22. A transgenic plant according to claim 21 wherein the plant is a conifer.

23. An isolated nucleic acid molecule comprising at least 30 contiguous nucleotides of the sequence shown in Seq. I.D. No. 6.

24. A recombinant nucleic acid molecule comprising a promoter sequence operably linked to a nucleic acid sequence according to claim 23, wherein the nucleic acid molecule is operably linked to the promoter sequence in sense or antisense orientation.

25. A microbial or plant cell transformed with a recombinant nucleic acid molecule according to claim 24.

26. A transgenic plant comprising a recombinant nucleic acid molecule according to claim 24.

27. A transgenic plant according to claim 26 wherein the plant is a conifer.

28. A transgenic plant according to claim 26 wherein the plant is a Pinus species.

29. An isolated nucleic acid molecule comprising at least 50 contiguous nucleotides of the sequence shown in Seq. I.D. No. 6.

30. A recombinant nucleic acid molecule comprising a promoter sequence operably linked to a nucleic acid sequence according to claim 29, wherein the nucleic acid molecule is operably linked to the promoter sequence in sense or antisense orientation.

31. A microbial or plant cell transformed with a recombinant nucleic acid molecule according to claim 30.

32. A transgenic plant comprising a recombinant nucleic acid molecule according to claim 30.

33. A transgenic plant according to claim 32 wherein the plant is a conifer.

34. A transgenic plant according to claim 32 wherein the plant is a Pinus species.

35. An isolated nucleic acid molecule comprising at least 100 contiguous nucleotides of the sequence shown in Seq. I.D. No. 6.

36. A recombinant nucleic acid molecule comprising a promoter sequence operably linked to a nucleic acid sequence according to claim 35, wherein the nucleic acid molecule is operably linked to the promoter sequence in sense or antisense orientations 37. A microbial or plant cell transformed with a recombinant nucleic acid molecule according to claim 36.

38. A transgenic plant comprising a recombinant nucleic acid molecule according to claim 36.

39. A transgenic plant according to claim 38 wherein the plant is a conifer.

40. A transgenic plant according to claim 38 wherein the plant is a Pinus species.

* * * * *

SEQUENCE LISTING

```
<160> NUMBER OF SEQ ID NOS: 14

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence:primer N7A
<220> FEATURE:
<221> NAME/KEY: modified_base
<222> LOCATION: (16)
<223> OTHER INFORMATION: The letter 'n' in this sequence (position 16)
      is an inosine (i)

<400> SEQUENCE: 1
gctctagagc gaymgnaaya aytttcc                                            27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:primer N7B
<220> FEATURE:
```

-continued

```
<221> NAME/KEY: modified_base
<222> LOCATION: (16)
<223> OTHER INFORMATION: The letter 'n' in this sequence (position 16)
      is an inosine (i)

<400> SEQUENCE: 2
gctctagagc gaymgnaaya ayttccc                                         27

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:primer N10
<220> FEATURE:
<221> NAME/KEY: modified_base
<222> LOCATION: (6,18,21)
<223> OTHER INFORMATION: The letter 'n' in this sequence (positions
      6,18,and 21) are inosine (i)

<400> SEQUENCE: 3
gaymgnaaya ayttcccnws ngwtt                                           25

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:primer
      CBG172

<400> SEQUENCE: 4
cacatatctg tgatattggt cg                                              22

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:primer CBG75

<400> SEQUENCE: 5
ccatcttctc ggactgctc                                                  19

<210> SEQ ID NO 6
<211> LENGTH: 1909
<212> TYPE: DNA
<213> ORGANISM: Pinus contorta
<220> FEATURE:
<221> NAME/KEY: CDS
<222> LOCATION: (183)..(1724)

<400> SEQUENCE: 6
ggatttggac ctgaaaatat caatttcaaa gcaattccag agggataacg tgggatcctt     60
accattacca acaacccacc attccgccct gccgacctca ggcatatttt gattctattt    120
aaccattaat tcatctgggc agttgtgatt ctgtataatt cgatcgctcc gttttagcag    180 ac atg gag gtg tct gtg ttg atg tgg gta ctg ctc ttc tat tcc tta      227
   Met Glu Val Ser Val Leu Met Trp Val Leu Leu Phe Tyr Ser Leu
    1               5                  10                  15 tta ggt ttt caa gtg acg aca gct agg ctg gac agg aac aac ttc ccc     275
Leu Gly Phe Gln Val Thr Thr Ala Arg Leu Asp Arg Asn Asn Phe Pro
             20                  25                  30 tca gat ttc atg ttc ggc aca gcc tct tca gcg tat cag tat gaa gga     323
Ser Asp Phe Met Phe Gly Thr Ala Ser Ser Ala Tyr Gln Tyr Glu Gly
         35                  40                  45
```

-continued

| | | |
|---|---|---|
| gca gtc cga gaa gat ggc aag ggt cct agc aca tgg gac gcc tta aca<br>Ala Val Arg Glu Asp Gly Lys Gly Pro Ser Thr Trp Asp Ala Leu Thr<br>     50                     55                      60 | 371 |
| cat atg cct ggt aga ata aaa gat agc agc aat gga gac gtg gca gtc<br>His Met Pro Gly Arg Ile Lys Asp Ser Ser Asn Gly Asp Val Ala Val<br> 65                      70                      75 | 419 |
| gac caa tat cac aga tat atg gaa gat atc gag ctt atg gct tca ctt<br>Asp Gln Tyr His Arg Tyr Met Glu Asp Ile Glu Leu Met Ala Ser Leu<br> 80                      85                      90                      95 | 467 |
| gga cta gat gcc tat aga ttc tcc ata tcc tgg tct cga atc ctt cca<br>Gly Leu Asp Ala Tyr Arg Phe Ser Ile Ser Trp Ser Arg Ile Leu Pro<br>                     100                    105                   110 | 515 |
| gaa gga aga ggt gaa att aac atg gct ggg att gaa tat tac aat aat<br>Glu Gly Arg Gly Glu Ile Asn Met Ala Gly Ile Glu Tyr Tyr Asn Asn<br>              115                    120                    125 | 563 |
| ctg att gac gct ctt ctg caa aat ggg atc cag ccg ttc gtg aca ttg<br>Leu Ile Asp Ala Leu Leu Gln Asn Gly Ile Gln Pro Phe Val Thr Leu<br>130                       135                    140 | 611 |
| ttc cat ttc gat ctt ccc aaa gca ctt gaa gac tcc tat ggg gga tgg<br>Phe His Phe Asp Leu Pro Lys Ala Leu Glu Asp Ser Tyr Gly Gly Trp<br>     145                    150                    155 | 659 |
| ctg agt cct caa ata att aac gac ttc gaa gcc tat gca gag att tgc<br>Leu Ser Pro Gln Ile Ile Asn Asp Phe Glu Ala Tyr Ala Glu Ile Cys<br>160                       165                    170                    175 | 707 |
| ttc cgg gca ttc ggt gac cgt gtc aaa tat tgg gcg aca gtg aac gag<br>Phe Arg Ala Phe Gly Asp Arg Val Lys Tyr Trp Ala Thr Val Asn Glu<br>                     180                    185                   190 | 755 |
| cca aat ctg ttt gtg ccg ttg gga tac acc gtc gga ata ttt cca ccg<br>Pro Asn Leu Phe Val Pro Leu Gly Tyr Thr Val Gly Ile Phe Pro Pro<br>              195                    200                    205 | 803 |
| acg agg tgt gct gcc cct cac gcc aat cct ttg tgc atg aca ggg aat<br>Thr Arg Cys Ala Ala Pro His Ala Asn Pro Leu Cys Met Thr Gly Asn<br>             210                    215                    220 | 851 |
| tgc tcg tca gca gag cca tat cta gct gca cat cac gtt ttg ctc gcc<br>Cys Ser Ser Ala Glu Pro Tyr Leu Ala Ala His His Val Leu Leu Ala<br>225                       230                    235 | 899 |
| cac gca tct gca gtg gag aaa tat agg gag aaa tat cag aaa att caa<br>His Ala Ser Ala Val Glu Lys Tyr Arg Glu Lys Tyr Gln Lys Ile Gln<br>240                       245                    250                    255 | 947 |
| gga gga tct ata ggg tta gtt ata agc gcg cca tgg tac gaa ccc ttg<br>Gly Gly Ser Ile Gly Leu Val Ile Ser Ala Pro Trp Tyr Glu Pro Leu<br>             260                    265                    270 | 995 |
| gaa aat tct cca gaa gag aga tca gct gtt gat aga att tta tcc ttc<br>Glu Asn Ser Pro Glu Glu Arg Ser Ala Val Asp Arg Ile Leu Ser Phe<br>          275                    280                    285 | 1043 |
| aat ctc cga tgg ttt ttg gat cca att gtt ttt gga gat tat cca caa<br>Asn Leu Arg Trp Phe Leu Asp Pro Ile Val Phe Gly Asp Tyr Pro Gln<br>        290                    295                    300 | 1091 |
| gaa atg cgt gaa aga tta gga tcg cgc tta ccc tcc ata tcc tcg gaa<br>Glu Met Arg Glu Arg Leu Gly Ser Arg Leu Pro Ser Ile Ser Ser Glu<br>305                       310                    315 | 1139 |
| cta tct gcg aaa ctt cgg gga tcg ttc gac tat atg ggt att aat cac<br>Leu Ser Ala Lys Leu Arg Gly Ser Phe Asp Tyr Met Gly Ile Asn His<br>320                       325                    330                    335 | 1187 |
| tat aca acc tta tat gca aca agc act cct ccc ctt tcc ccc gac cac<br>Tyr Thr Thr Leu Tyr Ala Thr Ser Thr Pro Pro Leu Ser Pro Asp His<br>             340                    345                    350 | 1235 |
| acg caa tat cta tat cca gac tct agg gtt tat ctg act gga gag cgc<br>Thr Gln Tyr Leu Tyr Pro Asp Ser Arg Val Tyr Leu Thr Gly Glu Arg<br>                355                    360                    365 | 1283 |

```
cac gga gtc tcc atc gga gaa cgg aca ggg atg gac ggt ttg ttt gtg    1331
His Gly Val Ser Ile Gly Glu Arg Thr Gly Met Asp Gly Leu Phe Val
            370                 375                 380 gta cct cat gga att caa aaa ata gtg gag tat gta aaa gaa ttc tat    1379
Val Pro His Gly Ile Gln Lys Ile Val Glu Tyr Val Lys Glu Phe Tyr
    385                 390                 395 gac aac ccg act att att atc gca gag aac ggt tat cca gag tct gag    1427
Asp Asn Pro Thr Ile Ile Ile Ala Glu Asn Gly Tyr Pro Glu Ser Glu
400                 405                 410                 415 gaa tcc tcg tcg act ctg caa gaa aat cta aac gat gtg agg aga ata    1475
Glu Ser Ser Ser Thr Leu Gln Glu Asn Leu Asn Asp Val Arg Arg Ile
                420                 425                 430 agg ttt cat gga gat tgt ttg agt tat ctc agt gca gca atc aaa aat    1523
Arg Phe His Gly Asp Cys Leu Ser Tyr Leu Ser Ala Ala Ile Lys Asn
            435                 440                 445 ggc tca gat gtt cga ggg tac ttt gtg tgg tca ctt ctg gat aat ttt    1571
Gly Ser Asp Val Arg Gly Tyr Phe Val Trp Ser Leu Leu Asp Asn Phe
        450                 455                 460 gag tgg gca ttt ggg tat acc att aga ttt ggt ctt tat cac gtg gat    1619
Glu Trp Ala Phe Gly Tyr Thr Ile Arg Phe Gly Leu Tyr His Val Asp
465                 470                 475 ttc att tct gat caa aag aga tat ccc aag ctc tcg gct caa tgg ttc    1667
Phe Ile Ser Asp Gln Lys Arg Tyr Pro Lys Leu Ser Ala Gln Trp Phe
480                 485                 490                 495 aga caa ttt ctt cag cac gac gat cag gga agt att aga agc agc agc    1715
Arg Gln Phe Leu Gln His Asp Asp Gln Gly Ser Ile Arg Ser Ser Ser
                500                 505                 510 agc att tag actgcgttgt ctatttgcta atcaaagcgc acacattcct            1764
Ser Ile gcaactctac ccaaaatcct gcaagcaaat atgttgtgtt cggatctatc caccgtgaga  1824
cacattacaa agaaatcatc aatctattcc aaaatgcaga aaaccccatt cagatgttct  1884
agggaactgc agggtaagaa cattg                                        1909

<210> SEQ ID NO 7
<211> LENGTH: 513
<212> TYPE: PRT
<213> ORGANISM: Pinus contorta

<400> SEQUENCE: 7

Met Glu Val Ser Val Leu Met Trp Val Leu Leu Phe Tyr Ser Leu Leu
 1               5                  10                  15

Gly Phe Gln Val Thr Thr Ala Arg Leu Asp Arg Asn Asn Phe Pro Ser
                20                  25                  30

Asp Phe Met Phe Gly Thr Ala Ser Ser Ala Tyr Gln Tyr Glu Gly Ala
            35                  40                  45

Val Arg Glu Asp Gly Lys Gly Pro Ser Thr Trp Asp Ala Leu Thr His
        50                  55                  60

Met Pro Gly Arg Ile Lys Asp Ser Ser Asn Gly Asp Val Ala Val Asp
65                  70                  75                  80

Gln Tyr His Arg Tyr Met Glu Asp Ile Glu Leu Met Ala Ser Leu Gly
                85                  90                  95

Leu Asp Ala Tyr Arg Phe Ser Ile Ser Trp Ser Arg Ile Leu Pro Glu
            100                 105                 110

Gly Arg Gly Glu Ile Asn Met Ala Gly Ile Glu Tyr Tyr Asn Asn Leu
        115                 120                 125

Ile Asp Ala Leu Leu Gln Asn Gly Ile Gln Pro Phe Val Thr Leu Phe
    130                 135                 140
```

```
His Phe Asp Leu Pro Lys Ala Leu Glu Asp Ser Tyr Gly Gly Trp Leu
145                 150                 155                 160

Ser Pro Gln Ile Ile Asn Asp Phe Glu Ala Tyr Ala Glu Ile Cys Phe
                165                 170                 175

Arg Ala Phe Gly Asp Arg Val Lys Tyr Trp Ala Thr Val Asn Glu Pro
            180                 185                 190

Asn Leu Phe Val Pro Leu Gly Tyr Thr Val Gly Ile Phe Pro Pro Thr
        195                 200                 205

Arg Cys Ala Ala Pro His Ala Asn Pro Leu Cys Met Thr Gly Asn Cys
210                 215                 220

Ser Ser Ala Glu Pro Tyr Leu Ala Ala His His Val Leu Leu Ala His
225                 230                 235                 240

Ala Ser Ala Val Glu Lys Tyr Arg Glu Lys Tyr Gln Lys Ile Gln Gly
                245                 250                 255

Gly Ser Ile Gly Leu Val Ile Ser Ala Pro Trp Tyr Glu Pro Leu Glu
            260                 265                 270

Asn Ser Pro Glu Glu Arg Ser Ala Val Asp Arg Ile Leu Ser Phe Asn
        275                 280                 285

Leu Arg Trp Phe Leu Asp Pro Ile Val Phe Gly Asp Tyr Pro Gln Glu
290                 295                 300

Met Arg Glu Arg Leu Gly Ser Arg Leu Pro Ser Ile Ser Ser Glu Leu
305                 310                 315                 320

Ser Ala Lys Leu Arg Gly Ser Phe Asp Tyr Met Gly Ile Asn His Tyr
                325                 330                 335

Thr Thr Leu Tyr Ala Thr Ser Thr Pro Pro Leu Ser Pro Asp His Thr
            340                 345                 350

Gln Tyr Leu Tyr Pro Asp Ser Arg Val Tyr Leu Thr Gly Glu Arg His
        355                 360                 365

Gly Val Ser Ile Gly Glu Arg Thr Gly Met Asp Gly Leu Phe Val Val
370                 375                 380

Pro His Gly Ile Gln Lys Ile Val Glu Tyr Val Lys Glu Phe Tyr Asp
385                 390                 395                 400

Asn Pro Thr Ile Ile Ile Ala Glu Asn Gly Tyr Pro Glu Ser Glu Glu
                405                 410                 415

Ser Ser Ser Thr Leu Gln Glu Asn Leu Asn Asp Val Arg Arg Ile Arg
            420                 425                 430

Phe His Gly Asp Cys Leu Ser Tyr Leu Ser Ala Ala Ile Lys Asn Gly
        435                 440                 445

Ser Asp Val Arg Gly Tyr Phe Val Trp Ser Leu Leu Asp Asn Phe Glu
450                 455                 460

Trp Ala Phe Gly Tyr Thr Ile Arg Phe Gly Leu Tyr His Val Asp Phe
465                 470                 475                 480

Ile Ser Asp Gln Lys Arg Tyr Pro Lys Leu Ser Ala Gln Trp Phe Arg
                485                 490                 495

Gln Phe Leu Gln His Asp Asp Gln Gly Ser Ile Arg Ser Ser Ser Ser
            500                 505                 510

Ile
```

<210> SEQ ID NO 8
<211> LENGTH: 1542
<212> TYPE: DNA
<213> ORGANISM: Pinus contorta
<220> FEATURE:
<221> NAME/KEY: CDS
<222> LOCATION: (1)..(1542)

-continued

<400> SEQUENCE: 8

```
atg gag gtg tct gtg ttg atg tgg gta ctg ctc ttc tat tcc tta tta      48
Met Glu Val Ser Val Leu Met Trp Val Leu Leu Phe Tyr Ser Leu Leu
 1               5                  10                  15 ggt ttt caa gtg acg aca gct agg ctg gac agg aac aac ttc ccc tca      96
Gly Phe Gln Val Thr Thr Ala Arg Leu Asp Arg Asn Asn Phe Pro Ser
             20                  25                  30 gat ttc atg ttc ggc aca gcc tct tca gcg tat cag tat gaa gga gca     144
Asp Phe Met Phe Gly Thr Ala Ser Ser Ala Tyr Gln Tyr Glu Gly Ala
         35                  40                  45 gtc cga gaa gat ggc aag ggt cct agc aca tgg gac gcc tta aca cat     192
Val Arg Glu Asp Gly Lys Gly Pro Ser Thr Trp Asp Ala Leu Thr His
 50                  55                  60 atg cct ggt aga ata aaa gat agc agc aat gga gac gtg gca gtc gac     240
Met Pro Gly Arg Ile Lys Asp Ser Ser Asn Gly Asp Val Ala Val Asp
 65                  70                  75                  80 caa tat cac aga tat atg gaa gat atc gag ctt atg gct tca ctt gga     288
Gln Tyr His Arg Tyr Met Glu Asp Ile Glu Leu Met Ala Ser Leu Gly
                 85                  90                  95 cta gat gcc tat aga ttc tcc ata tcc tgg tct cga atc ctt cca gaa     336
Leu Asp Ala Tyr Arg Phe Ser Ile Ser Trp Ser Arg Ile Leu Pro Glu
            100                 105                 110 gga aga ggt gaa att aac atg gct ggg att gaa tat tac aat aat ctg     384
Gly Arg Gly Glu Ile Asn Met Ala Gly Ile Glu Tyr Tyr Asn Asn Leu
        115                 120                 125 att gac gct ctt ctg caa aat ggg atc cag ccg ttc gtg aca ttg ttc     432
Ile Asp Ala Leu Leu Gln Asn Gly Ile Gln Pro Phe Val Thr Leu Phe
    130                 135                 140 cat ttc gat ctt ccc aaa gca ctt gaa gac tcc tat ggg gga tgg ctg     480
His Phe Asp Leu Pro Lys Ala Leu Glu Asp Ser Tyr Gly Gly Trp Leu
145                 150                 155                 160 agt cct caa ata att aac gac ttc gaa gcc tat gca gag att tgc ttc     528
Ser Pro Gln Ile Ile Asn Asp Phe Glu Ala Tyr Ala Glu Ile Cys Phe
                165                 170                 175 cgg gca ttc ggt gac cgt gtc aaa tat tgg gcg aca gtg aac gag cca     576
Arg Ala Phe Gly Asp Arg Val Lys Tyr Trp Ala Thr Val Asn Glu Pro
            180                 185                 190 aat ctg ttt gtg ccg ttg gga tac acc gtc gga ata ttt cca ccg acg     624
Asn Leu Phe Val Pro Leu Gly Tyr Thr Val Gly Ile Phe Pro Pro Thr
        195                 200                 205 agg tgt gct gcc cct cac gcc aat cct ttg tgc atg aca ggg aat tgc     672
Arg Cys Ala Ala Pro His Ala Asn Pro Leu Cys Met Thr Gly Asn Cys
    210                 215                 220 tcg tca gca gag cca tat cta gct gca cat cac gtt ttg ctc gcc cac     720
Ser Ser Ala Glu Pro Tyr Leu Ala Ala His His Val Leu Leu Ala His
225                 230                 235                 240 gca tct gca gtg gag aaa tat agg gag aaa tat cag aaa att caa gga     768
Ala Ser Ala Val Glu Lys Tyr Arg Glu Lys Tyr Gln Lys Ile Gln Gly
                245                 250                 255 gga tct ata ggg tta gtt ata agc gcg cca tgg tac gaa ccc ttg gaa     816
Gly Ser Ile Gly Leu Val Ile Ser Ala Pro Trp Tyr Glu Pro Leu Glu
            260                 265                 270 aat tct cca gaa gag aga tca gct gtt gat aga att tta tcc ttc aat     864
Asn Ser Pro Glu Glu Arg Ser Ala Val Asp Arg Ile Leu Ser Phe Asn
        275                 280                 285 ctc cga tgg ttt ttg gat cca att gtt ttt gga gat tat cca caa gaa     912
Leu Arg Trp Phe Leu Asp Pro Ile Val Phe Gly Asp Tyr Pro Gln Glu
    290                 295                 300 atg cgt gaa aga tta gga tcg cgc tta ccc tcc ata tcc tcg gaa cta     960
Met Arg Glu Arg Leu Gly Ser Arg Leu Pro Ser Ile Ser Ser Glu Leu
```

```
                305                 310                 315                 320
tct gcg aaa ctt cgg gga tcg ttc gac tat atg ggt att aat cac tat          1008
Ser Ala Lys Leu Arg Gly Ser Phe Asp Tyr Met Gly Ile Asn His Tyr
                325                 330                 335 aca acc tta tat gca aca agc act cct ccc ctt tcc ccc gac cac acg          1056
Thr Thr Leu Tyr Ala Thr Ser Thr Pro Pro Leu Ser Pro Asp His Thr
                340                 345                 350 caa tat cta tat cca gac tct agg gtt tat ctg act gga gag cgc cac          1104
Gln Tyr Leu Tyr Pro Asp Ser Arg Val Tyr Leu Thr Gly Glu Arg His
                355                 360                 365 gga gtc tcc atc gga gaa cgg aca ggg atg gac ggt ttg ttt gtg gta          1152
Gly Val Ser Ile Gly Glu Arg Thr Gly Met Asp Gly Leu Phe Val Val
        370                 375                 380 cct cat gga att caa aaa ata gtg gag tat gta aaa gaa ttc tat gac          1200
Pro His Gly Ile Gln Lys Ile Val Glu Tyr Val Lys Glu Phe Tyr Asp
385                 390                 395                 400 aac ccg act att att atc gca gag aac ggt tat cca gag tct gag gaa          1248
Asn Pro Thr Ile Ile Ile Ala Glu Asn Gly Tyr Pro Glu Ser Glu Glu
                405                 410                 415 tcc tcg tcg act ctg caa gaa aat cta aac gat gtg agg aga ata agg          1296
Ser Ser Ser Thr Leu Gln Glu Asn Leu Asn Asp Val Arg Arg Ile Arg
                420                 425                 430 ttt cat gga gat tgt ttg agt tat ctc agt gca gca atc aaa aat ggc          1344
Phe His Gly Asp Cys Leu Ser Tyr Leu Ser Ala Ala Ile Lys Asn Gly
                435                 440                 445 tca gat gtt cga ggg tac ttt gtg tgg tca ctt ctg gat aat ttt gag          1392
Ser Asp Val Arg Gly Tyr Phe Val Trp Ser Leu Leu Asp Asn Phe Glu
        450                 455                 460 tgg gca ttt ggg tat acc att aga ttt ggt ctt tat cac gtg gat ttc          1440
Trp Ala Phe Gly Tyr Thr Ile Arg Phe Gly Leu Tyr His Val Asp Phe
465                 470                 475                 480 att tct gat caa aag aga tat ccc aag ctc tcg gct caa tgg ttc aga          1488
Ile Ser Asp Gln Lys Arg Tyr Pro Lys Leu Ser Ala Gln Trp Phe Arg
                485                 490                 495 caa ttt ctt cag cac gac gat cag gga agt att aga agc agc agc agc          1536
Gln Phe Leu Gln His Asp Asp Gln Gly Ser Ile Arg Ser Ser Ser Ser
                500                 505                 510 att tag                                                                   1542
Ile <210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:primer NT1

<400> SEQUENCE: 9
tagctagcag gctggacagg aacaacttc                                            29

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:primer CT1

<400> SEQUENCE: 10
ctcgagacaa gcagtctaaa tgct                                                 24

<210> SEQ ID NO 11
<211> LENGTH: 24
```

-continued

```
<212> TYPE: DNA
<213> ORGANISM: Artificial Sequence
<220> FEATURE:
<223> OTHER INFORMATION: Description of Artificial Sequence:primer for
      amplification of the CBG cDNA sequence

<400> SEQUENCE: 11
ggatttggac ctgaaaatat caat                                          24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:primer for
      the amplification of the CBG cDNA sequence

<400> SEQUENCE: 12
caatgttctt accctgcagt tccc                                          24

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:primer for
      the amplification of the CBG cDNA sequence

<400> SEQUENCE: 13
atggaggtgt ctgtgttgat gtgggta                                       27

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:primer for
      the amplification of the CBG cDNA sequence

<400> SEQUENCE: 14
aatgctgctg ctgcttctaa tacttcc                                       27
```